US007720521B2

(12) United States Patent
Chang et al.

(10) Patent No.: US 7,720,521 B2
(45) Date of Patent: May 18, 2010

(54) METHODS AND DEVICES FOR PERFORMING PROCEDURES WITHIN THE EAR, NOSE, THROAT AND PARANASAL SINUSES

(75) Inventors: John Y. Chang, Mountain View, CA (US); Joshua Makower, Los Altos, CA (US); Julia D. Vrany, Sunnyvale, CA (US); John H. Morriss, Portola Valley, CA (US); Ketan P. Muni, San Jose, CA (US)

(73) Assignee: Acclarent, Inc., Menlo Park, CA (US)

( * ) Notice: Subject to any disclaimer, the term of this patent is extended or adjusted under 35 U.S.C. 154(b) by 1419 days.

(21) Appl. No.: 11/116,118

(22) Filed: Apr. 26, 2005

(65) Prior Publication Data

US 2006/0004286 A1 Jan. 5, 2006

Related U.S. Application Data

(63) Continuation-in-part of application No. 10/829,917, filed on Apr. 21, 2004, and a continuation-in-part of application No. 10/912,578, filed on Aug. 4, 2004, now Pat. No. 7,361,168, and a continuation-in-part of application No. 10/944,270, filed on Sep. 17, 2004, and a continuation-in-part of application No. 11/037,548, filed on Jan. 18, 2005, now Pat. No. 7,462,175.

(51) Int. Cl.
*A61B 1/00* (2006.01)
*A61B 1/32* (2006.01)

(52) U.S. Cl. .................. 600/424; 600/427; 600/407; 600/199

(58) Field of Classification Search ............... 600/429, 600/117, 407; 606/196–199; 604/54, 96
See application file for complete search history.

(56) References Cited

U.S. PATENT DOCUMENTS

| 504,424 A | 9/1893 | De Pezzer |
| 705,346 A | 7/1902 | Hamilton |
| 2,525,183 A | 10/1950 | Robison |
| 3,173,418 A | 3/1965 | Baran |
| 3,469,578 A | 9/1969 | Bierman |
| 3,486,539 A | 12/1969 | Jacuzzi |

(Continued)

FOREIGN PATENT DOCUMENTS

CH 668188 12/1988

(Continued)

OTHER PUBLICATIONS

Göttman, et al.; Balloon Dilation of Recurrent Ostial Occlusion of the frontal sinus; Abstract No. B-04353, European Congress of Radiology, Mar. 2001.

(Continued)

*Primary Examiner*—Eric F Winakur
*Assistant Examiner*—Lawrence N Laryea
(74) *Attorney, Agent, or Firm*—Steptoe & Johnson LLP

(57) ABSTRACT

Devices, systems and methods for performing image guided interventional and surgical procedures, including various procedures to treat sinusitis and other disorders of the paranasal sinuses, ears, nose or throat.

86 Claims, 13 Drawing Sheets

U.S. PATENT DOCUMENTS

| | | |
|---|---|---|
| 3,506,005 A | 4/1970 | Gilio et al. |
| 3,527,220 A | 9/1970 | Summers |
| 3,800,788 A | 4/1974 | White |
| 3,859,993 A | 1/1975 | Betner |
| 3,921,636 A | 11/1975 | Zaffaroni |
| 3,948,254 A | 4/1976 | Zaffaroni |
| 3,948,262 A | 4/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,102,342 A | 7/1978 | Akiyama et al. |
| 4,184,497 A | 1/1980 | Kolff et al. |
| 4,207,890 A | 6/1980 | Mamajek et al. |
| 4,217,898 A | 8/1980 | Theeuwes |
| 4,338,941 A | 7/1982 | Payton |
| 4,437,856 A | 3/1984 | Valli |
| 4,637,389 A | 1/1987 | Heyden |
| 4,669,469 A | 6/1987 | Gifford et al. |
| 4,708,434 A | 11/1987 | Tsuno |
| 4,708,834 A | 11/1987 | Cohen et al. |
| 4,737,141 A | 4/1988 | Spits |
| 4,748,969 A | 6/1988 | Wardle |
| 4,755,171 A | 7/1988 | Tennant |
| 4,811,743 A | 3/1989 | Stevens |
| 4,815,478 A | 3/1989 | Buchbinder et al. |
| 4,851,228 A | 7/1989 | Zentner et al. |
| 4,883,465 A | 11/1989 | Brennan |
| 4,898,577 A | 2/1990 | Badger et al. |
| 4,919,112 A | 4/1990 | Siegmund |
| 4,998,916 A | 3/1991 | Hammerslag et al. |
| 5,021,043 A | 6/1991 | Becker et al. |
| 5,026,384 A | 6/1991 | Farr et al. |
| 5,087,244 A | 2/1992 | Wolinsky et al. |
| 5,127,393 A | 7/1992 | McFarlin et al. |
| 5,139,832 A | 8/1992 | Hayashi et al. |
| 5,152,747 A | 10/1992 | Olivier |
| 5,167,220 A | 12/1992 | Brown |
| 5,168,864 A | 12/1992 | Shockey |
| 5,169,386 A | 12/1992 | Becker et al. |
| 5,171,233 A | 12/1992 | Amplatz et al. |
| 5,207,695 A | 5/1993 | Trout, III |
| 5,250,059 A | 10/1993 | Andreas et al. |
| 5,251,092 A | 10/1993 | Brady et al. |
| 5,255,679 A | 10/1993 | Imran |
| 5,264,260 A | 11/1993 | Saab |
| 5,304,123 A | 4/1994 | Atala et al. |
| 5,336,163 A | 8/1994 | DeMane et al. |
| 5,343,865 A | 9/1994 | Gardineer et al. |
| 5,346,075 A | 9/1994 | Nichols et al. |
| 5,356,418 A | 10/1994 | Shturman |
| 5,368,566 A | 11/1994 | Crocker |
| 5,415,633 A | 5/1995 | Lazarus et al. |
| 5,425,370 A | 6/1995 | Vilkomerson |
| 5,439,446 A | 8/1995 | Barry |
| 5,441,497 A | 8/1995 | Narciso, Jr. |
| 5,451,221 A | 9/1995 | Cho et al. |
| 5,454,817 A | 10/1995 | Katz |
| 5,465,717 A | 11/1995 | Imran et al. |
| 5,496,338 A | 3/1996 | Miyagi et al. |
| 5,507,725 A | 4/1996 | Savage et al. |
| 5,512,055 A | 4/1996 | Domb et al. |
| 5,519,532 A | 5/1996 | Broome |
| 5,546,964 A | 8/1996 | Stangerup |
| 5,558,073 A | 9/1996 | Pomeranz et al. |
| 5,568,809 A | 10/1996 | Ben-haim |
| 5,578,007 A | 11/1996 | Imran |
| 5,578,048 A | 11/1996 | Pasqualucci et al. |
| 5,601,594 A | 2/1997 | Best |
| 5,634,908 A | 6/1997 | Loomas |
| 5,645,789 A | 7/1997 | Roucher, Jr. |
| 5,647,361 A | 7/1997 | Damadian |
| 5,656,030 A | 8/1997 | Hunjan et al. |
| 5,664,567 A | 9/1997 | Linder |
| 5,669,388 A | 9/1997 | Vilkomerson |
| 5,685,838 A | 11/1997 | Peters et al. |
| 5,685,847 A | 11/1997 | Barry |
| 5,693,065 A | 12/1997 | Rains, III |
| 5,694,945 A | 12/1997 | Ben-Haim |
| 5,711,315 A * | 1/1998 | Jerusalmy .................. 128/898 |
| 5,713,946 A | 2/1998 | Ben-Haim |
| 5,718,702 A * | 2/1998 | Edwards ...................... 606/41 |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,752,513 A | 5/1998 | Acker et al. |
| 5,775,327 A | 7/1998 | Randolph et al. |
| 5,789,391 A | 8/1998 | Jacobus et al. |
| 5,820,568 A | 10/1998 | Willis |
| 5,827,224 A | 10/1998 | Shippert |
| 5,833,608 A | 11/1998 | Acker |
| 5,836,935 A | 11/1998 | Ashton et al. |
| 5,857,998 A | 1/1999 | Barry |
| 5,872,879 A | 2/1999 | Hamm |
| 5,902,247 A | 5/1999 | Coe et al. |
| 5,928,192 A | 7/1999 | Maahs |
| 5,931,818 A | 8/1999 | Werp et al. |
| 5,935,061 A | 8/1999 | Acker et al. |
| 5,947,988 A | 9/1999 | Smith |
| 5,949,929 A | 9/1999 | Hamm |
| 5,954,693 A | 9/1999 | Barry |
| 5,980,551 A | 11/1999 | Summers et al. |
| 5,985,307 A | 11/1999 | Hanson et al. |
| 5,997,562 A | 12/1999 | Zadno-Azizi et al. |
| 6,013,019 A | 1/2000 | Fischell et al. |
| 6,015,414 A | 1/2000 | Werp et al. |
| 6,048,299 A | 4/2000 | Hoffmann |
| 6,053,172 A | 4/2000 | Hovda |
| 6,083,188 A | 7/2000 | Becker |
| 6,109,268 A | 8/2000 | Thapliyal et al. |
| 6,113,567 A | 9/2000 | Becker |
| 6,142,957 A | 11/2000 | Diamond et al. |
| 6,148,823 A | 11/2000 | Hastings |
| 6,171,298 B1 | 1/2001 | Matsuura et al. |
| 6,171,303 B1 | 1/2001 | Ben-Haim et al. |
| 6,176,829 B1 | 1/2001 | Vilkomerson |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,195,225 B1 | 2/2001 | Komatsu et al. |
| 6,238,364 B1 | 5/2001 | Becker |
| 6,238,391 B1 | 5/2001 | Olsen et al. |
| 6,293,957 B1 | 9/2001 | Peters et al. |
| 6,302,875 B1 | 10/2001 | Makower et al. |
| 6,340,360 B1 | 1/2002 | Lyles et al. |
| 6,375,615 B1 | 4/2002 | Flaherty et al. |
| 6,394,093 B1 | 5/2002 | Lethi |
| 6,425,877 B1 | 7/2002 | Edwards |
| 6,432,986 B2 | 8/2002 | Levin |
| 6,468,202 B1 * | 10/2002 | Irion et al. .................. 600/117 |
| 6,468,297 B1 | 10/2002 | Williams et al. |
| 6,491,940 B1 | 12/2002 | Levin |
| 6,500,130 B2 | 12/2002 | Kinsella et al. |
| 6,503,185 B1 | 1/2003 | Waksman et al. |
| 6,536,437 B1 | 3/2003 | Dragisic |
| 6,544,230 B1 | 4/2003 | Flaherty et al. |
| 6,549,800 B1 | 4/2003 | Atalar |
| 6,551,239 B2 | 4/2003 | Renner et al. |
| 6,571,131 B1 | 5/2003 | Nguyen |
| 6,572,538 B2 | 6/2003 | Takase |
| 6,585,794 B2 | 7/2003 | Shimoda et al. |
| 6,596,009 B1 | 7/2003 | Jelic |
| 6,638,233 B2 | 10/2003 | Corvi et al. |

| | | |
|---|---|---|
| 6,663,589 B1 | 12/2003 | Halevy |
| 6,669,689 B2 | 12/2003 | Lehmann et al. |
| 6,685,648 B2 | 2/2004 | Flaherty et al. |
| 6,716,813 B2 | 4/2004 | Lim et al. |
| 6,776,772 B1 | 8/2004 | Vrijer et al. |
| 6,783,536 B2 | 8/2004 | Vilsmeier |
| D501,677 S | 2/2005 | Becker |
| 7,011,654 B2 | 3/2006 | Dubrul et al. |
| 7,022,105 B1 | 4/2006 | Edwards |
| 7,056,303 B2 | 6/2006 | Dennis et al. |
| 7,131,969 B1 | 11/2006 | Hovda et al. |
| D534,216 S | 12/2006 | Makower et al. |
| 7,169,163 B2 | 1/2007 | Becker |
| 7,442,191 B2 | 10/2008 | Hovda et al. |
| 7,454,244 B2 | 11/2008 | Kassab et al. |
| 7,462,175 B2 | 12/2008 | Chang et al. |
| 7,488,313 B2 | 2/2009 | Segal et al. |
| 2001/0027307 A1 | 10/2001 | Dubrul et al. |
| 2001/0029317 A1 | 10/2001 | Hayakawa |
| 2002/0165521 A1 | 11/2002 | Cioanta et al. |
| 2003/0130598 A1 | 7/2003 | Manning et al. |
| 2003/0181827 A1 | 9/2003 | Hojeibane et al. |
| 2003/0185872 A1 | 10/2003 | Kochinke |
| 2003/0208194 A1 | 11/2003 | Hovda et al. |
| 2004/0058992 A1 | 3/2004 | Marinello et al. |
| 2004/0064083 A1 | 4/2004 | Becker |
| 2004/0064150 A1 | 4/2004 | Becker |
| 2004/0116958 A1 | 6/2004 | Gopferich et al. |
| 2004/0249267 A1* | 12/2004 | Gilboa ........................ 600/424 |
| 2005/0049486 A1 | 3/2005 | Urquhart |
| 2005/0228412 A1* | 10/2005 | Surti ........................... 606/153 |
| 2005/0240147 A1 | 10/2005 | Makower |
| 2006/0004323 A1 | 1/2006 | Chang |
| 2006/0067982 A1 | 3/2006 | Haapakumpu et al. |
| 2006/0149310 A1* | 7/2006 | Becker ........................ 606/196 |
| 2006/0190022 A1 | 8/2006 | Beyar et al. |
| 2006/0210605 A1 | 9/2006 | Chang et al. |
| 2007/0005094 A1 | 1/2007 | Eaton et al. |
| 2007/0073269 A1 | 3/2007 | Becker |
| 2007/0129751 A1 | 6/2007 | Muni et al. |
| 2007/0135789 A1 | 6/2007 | Chang et al. |
| 2007/0208301 A1 | 9/2007 | Evard et al. |
| 2007/0250105 A1 | 10/2007 | Ressemann et al. |
| 2008/0097515 A1 | 4/2008 | Chang et al. |
| 2008/0125626 A1 | 5/2008 | Chang et al. |
| 2008/0195041 A1 | 8/2008 | Goldfarb et al. |

FOREIGN PATENT DOCUMENTS

| | | |
|---|---|---|
| CN | 2151720 U | 1/1994 |
| EP | 0129634 | 1/1985 |
| EP | 0418391 | 7/1991 |
| EP | 0585757 | 3/1994 |
| EP | 0624349 | 11/1994 |
| RU | 2213530 | 10/2003 |
| WO | WO90/11053 | 4/1990 |
| WO | WO91/17787 | 11/1991 |
| WO | WO 92/15286 | 9/1992 |
| WO | WO 96/29071 | 9/1996 |
| WO | WO 99/30655 | 6/1999 |
| WO | WO 00/53252 | 9/2000 |
| WO | WO 02/062269 | 8/2002 |
| WO | WO 03/105657 | 12/2003 |
| WO | WO 2004/006788 | 1/2004 |
| WO | WO 2004/018980 | 3/2004 |
| WO | WO 2004/116958 | 3/2004 |
| WO | WO 2004/082525 A2 | 9/2004 |
| WO | WO 2005/089670 | 9/2005 |
| WO | WO2006/107957 | 10/2006 |
| WO | WO 2008/051918 | 5/2008 |

OTHER PUBLICATIONS

Göttman, et al., Balloon dilatation of recurrent ostial occlusion of the front sinus; ECR, Mar. 2, 2001.

Göttman, et al., Successful Treatment of Recurrent Post-operative Frontal Sinus Stenoses by Balloon Dilatation; CIRSE, Oct. 5, 2002.

Göttman, et al., Balloon dilatation in the nasal cavity and paranasal sinuses; CIRSE, Sep. 25, 2004.

Robison, J. Mathews, M.D., Pressure Treatment of Purulent Maxillary Sinusitis, TEXAS State Journal of Medicine, May 1951, pp. 281-288.

Robison, J. Mathews, M.D., Pressure Treatment of Maxillary Sinusitis, J.A.M.A., May 31, 1952, pp. 436-440.

Strohm et al. Die Behandlung von Stenosen der oberen Luftwege mittels röntgenologisch gesteuerter Ballondilation Sep. 25, 1999.

Office Action dated Dec. 10, 2007 in U.S. Appl. No. 10/912,578.

Office Action dated Nov. 28, 2007 in U.S. Appl. No. 11/234,395.

International Search Report, PCT International Application No. PCT/US06/02004.

Lanza, Donald C., Postoperative Care and Avoiding Frontal Recess Stenosis, International Advanced Sinus Symposium, Jul. 21-24, 1993.

Strohm et al. Die Behandlung von Stenosen der obersen Lufwege mittels rontgenologisch gesteuerter Ballondilation Sep. 1999.

USPTO Office Action dated Oct. 29, 2008 in U.S. Appl. No. 11/347,147, filed Feb. 2, 2006.

USPTO Office Action dated Mar. 3, 2009 in U.S. Appl. No. 12/117,582, filed May 8, 2008.

USPTO Office Action dated Nov. 25, 2008 in U.S. Appl. No. 12/117,961, filed May 9, 2008.

USPTO Office Action dated Mar. 4, 2009 in U.S. Appl. No. 12/118,931, filed May 12, 2008.

USPTO Office Action dated Dec. 5, 2008 in U.S. Appl. No. 12/120,902, filed May 15, 2008.

Benninger, et al.; Adult Chronic Rhinosinusitis: definitions, diagnosis, epidemiology, and pathophysiology; Arch Otolarygol Head and Neck Sug; vol. 129, p. S1-S22; Sep. 2003.

Barrett, Steven; Be Wary of Neurocranial Restructuring (NCR). Chirobase (available at: http://www.chirobase.org/06DD/ncr.html) Jul. 2003.

Croix, et al.; "Genes Expressed in Human Tumor Endothelium"; Science vol. 289 pp. 1197-1202; May 2000.

Davis, Greg E., et al., A Complication From Neurocranial Restructuring; Arch Otolaryngol Head Neck Surg; vol. 129, p. 472-474; Apr. 2003.

Miller, et al., Management of Fractures of the Supraorbital Rim, the Journal of Trauma, vol. 18, No. 7, pp. 507-512, Jul. 1978.

Woog, et al., Paranasal Sinus Endoscopy and Orbital Fracture Repair, Arch Ophthalmol, vol. 116, May 1998, pp. 688-691.

Friedman, et al., Intraoperative and Postoperative Assessment of Frontal Sinus Patency by Transillumination, Laryngoscope 110: Apr. 2000, pp. 683-684.

Binner, et al., Fibre-Optic Transillumination of the Sinuses: A Comparison of the Value of Radiography and Transillumination in Antral Disease, Clinical Otolaryngology, 1978, 3, pp. 1-11.

Hybels, Transillumination During Osteoplastic Frontal Sinusotomy, The Laryngoscope 91: Sep. 1981, p. 1560.

Stammberger, et al., Special Endoscopic Anatomy of the Lateral Nasal Wall and Ethmoidal Sinuses, Functional Endoscopic Sinus Surgery, 1991, Ch. 3, pp. 49-87.K.

Kuhn, et al., The Agger Nasi Cell in Frontal Recess Obstruction: An Anatomic, Radiology and Clinical Correlation, Operative Techniques in Otolaryngology-Head and Neck Surgery, vol. 2, No. 4, 1991, pp. 226-231.

Bent et al., The Frontal Cell as a Cause of Frontal Sinus Obstruction, American Journal of Rhinology, vol. 8, No. 4, 1994, pp. 185-191.

Casiano, et al., Endoscopic Lothrop Procedure: The University of Miami Experience, American Journal of Rhinology, vol. 12, No. 5, 1998, pp. 335-339.

Min, Yang-Gi et al., Mucociliary Activity and Histopathology of Sinus Mucosa in Experimental Maxilary Sinusitis: A Comparison of Systemic Administration of Antibiotic and Antibiotic Delivery by Polylactic Acid Polymer, Laryngoscope, Aug. 1995, 105:835-842.

Deutschmann, R. et al., A Contribution to the Topical Treatment of [Maxillary] Sinusitis Preliminary Communication, Stomat DDR 26 (1976), 585-592.

Tarasov, D.I. et al., Application of Drugs Based on Polymers in the Treatment of Acute and Chronic Maxillary Sinusitis, Vestn Otorinolaringol. (1978), vol. 6, pp. 45-47.

Chien, Y.W et al., Nasal Systemic Drug Delivery, Drugs and the pharmaceutical sciences, vol. 39, pp. 60-63.

U.S. Appl. No. 10/829,917.
U.S. Appl. No. 10/912,578.
U.S. Appl. No. 10/944,270.
U.S. Appl. No. 11/037,548.

* cited by examiner

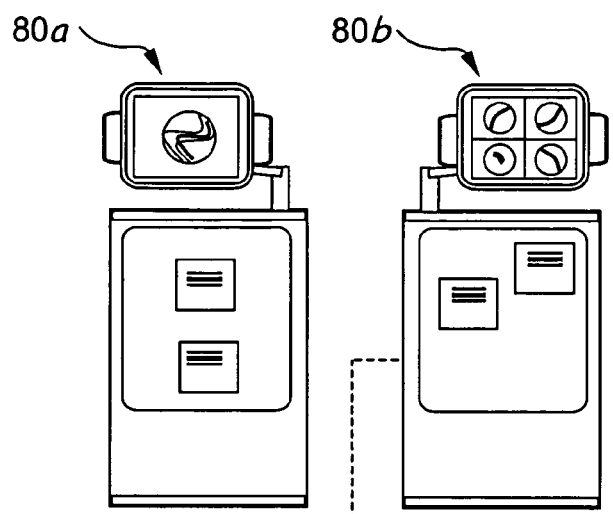
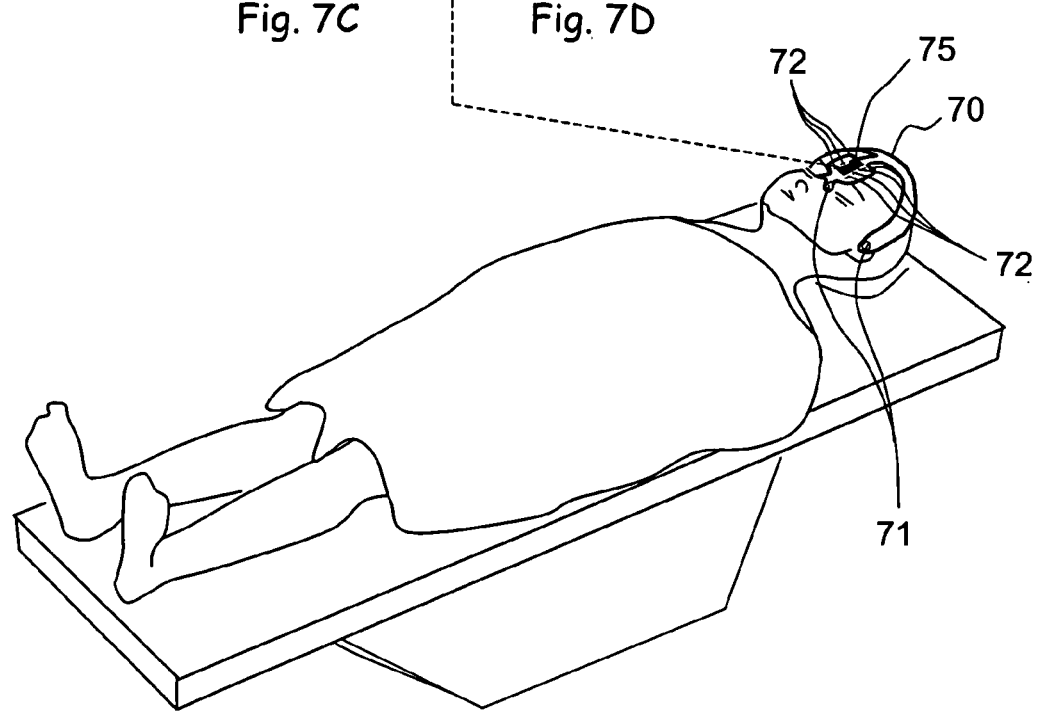
Fig. 7C    Fig. 7D
Fig. 7E

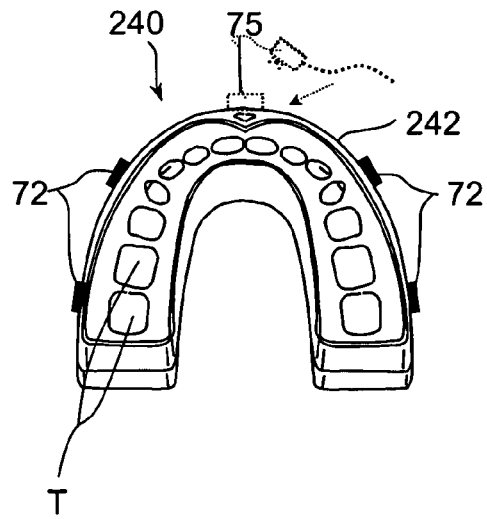
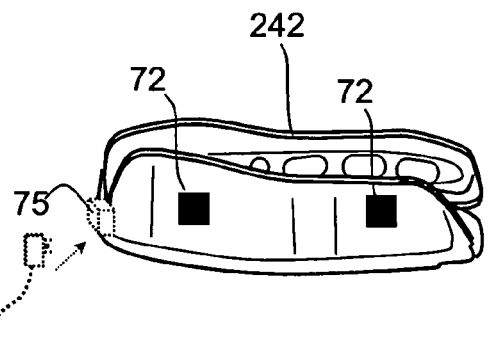
Fig. 14A          Fig. 14B
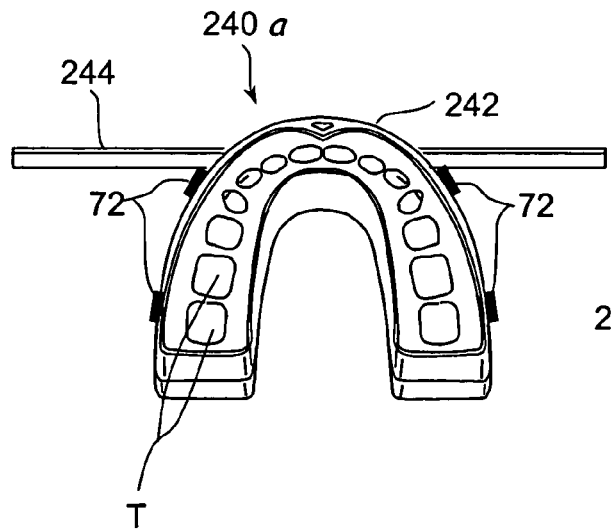
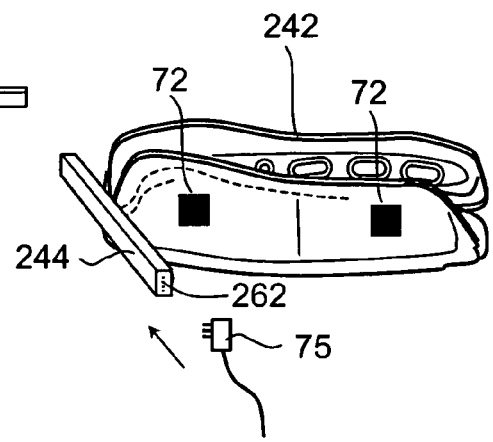
Fig. 15A          Fig. 15B
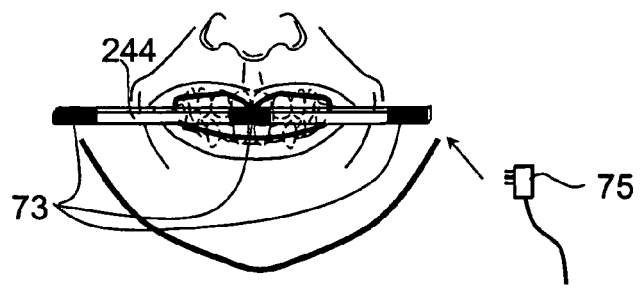
Fig. 15C

METHODS AND DEVICES FOR PERFORMING PROCEDURES WITHIN THE EAR, NOSE, THROAT AND PARANASAL SINUSES

RELATED APPLICATION

This application is a continuation-in-part of 1) U.S. patent application Ser. No. 10/829,917 entitled "Devices, Systems and Methods for Diagnosing and Treating Sinusitis and Other Disorders of the Ears, Nose and/or Throat" filed on Apr. 21, 2004, 2) U.S. patent application Ser. No. 10/912,578 entitled "Implantable Device and Methods for Delivering Drugs and Other Substances to Treat Sinusitis and Other Disorders" filed on Aug. 4, 2004, 3) U.S. patent application Ser. No. 10/944,270 entitled "Apparatus and Methods for Dilating and Modifying Ostia of Paranasal Sinuses and Other Intranasal or Paranasal Structures" filed on Sep. 17, 2004 and 4) U.S. patent application Ser. No. 11/037,548 entitled "Devices, Systems and Methods For Treating Disorders of the Ear, Nose and Throat" filed Jan. 18, 2005, the entireties of each such parent application being expressly incorporated herein by reference.

FIELD OF THE INVENTION

The present invention relates generally to medical devices, systems and methods and more particularly to methods and devices for performing image guided interventional procedures to treat disorders of the paranasal sinuses, ears, nose or throat (ENT).

BACKGROUND OF THE INVENTION

A. Recent Advancements in the Treatment of ENT Disorders

New devices, systems and techniques are being developed for the treatment of sinusitis and other disorders of the ear, nose, throat and paranasal sinuses. For example, various catheters, guidewires and other devices useable to perform minimally invasive, minimally traumatic ear, nose and throat surgery have been described in U.S. patent application Ser. No. 10/829,917 entitled "Devices, Systems and Methods for Diagnosing and Treating Sinusitis and Other Disorders of the Ears, Nose and/or Throat," Ser. No. 10/912,578 entitled "Implantable Device and Methods for Delivering Drugs and Other Substances to Treat Sinusitis and Other Disorders," Ser. No. 10/944,270 entitled "Apparatus and Methods for Dilating and Modifying Ostia of Paranasal Sinuses and Other Intranasal or Paranasal Structures" and Ser. No. 11/037,548 entitled "Devices, Systems and Methods For Treating Disorders of the Ear, Nose and Throat." Many of these new devices, systems and techniques are useable in conjunction with endoscopic, radiographic and/or electronic assistance to facilitate precise positioning and movement of catheters, guidewires and other devices within the ear, nose, throat and paranasal sinuses and to avoid undesirable trauma or damage to critical anatomical structures such as the eyes, facial nerves and brain.

For example, in one new procedure (referred to in this patent application as a "Flexible Transnasal Sinus Intervention" or FTSI), a dilation catheter (e.g., a balloon catheter or other type of dilator) is advanced through the nose to a position within the ostium of a paranasal sinus or other location, without requiring removal or surgical alteration of other intranasal anatomical structures. The dilation catheter is then used to dilate the ostium or other anatomical structures to facilitate natural drainage from the sinus cavity. In some cases, a tubular guide may be initially inserted through the nose and advanced to a position near the sinus ostium and a guidewire may then be advanced through the tubular guide and into the affected paranasal sinus. The dilation catheter may then be advanced over the guidewire and through the tubular guide to a position where its dilator (e.g., balloon) is positioned within the sinus ostium. The dilator (e.g., balloon) is then expanded causing the ostium to dilate. In some cases, such dilation of the ostium may fracture, move or remodel bony structures that surround or are adjacent to the ostium. Optionally, in some procedures, irrigation solution and/or therapeutic agents may be infused through a lumen of the dilation catheter and/or other working devices (e.g., guidewires, catheters, cannula, tubes, dilators, balloons, substance injectors, needles, penetrators, cutters, debriders, microdebriders, hemostatic devices, cautery devices, cryosurgical devices, heaters, coolers, scopes, endoscopes, light guides, phototherapy devices, drills, rasps, saws, etc.) may be advanced through the tubular guide and/or over the guidewire to deliver other therapy to the sinus or adjacent tissues during the same procedure in which the FTSI is carried out. It is to be understood that, in FTSI procedures, structures and passageways other than sinus ostia may be dilated using the tools described above, tissue may be resected or ablated, bone may be restructured, drugs or drug delivery systems may be deployed, etc., as described in the documents incorporated here by reference. Thus, for the purposes of this application the term FTSI will generally used to refer broadly to all of those procedures, not just dilation of sinus ostia.

B. Prior Uses of Image Guided Surgery in the Treatment of ENT Disorders

Image guided surgery (IGS) procedures (sometimes referred to as "computer assisted surgery") were first developed for use in neurosurgery and have now been adapted for use in certain ENT surgeries, including sinus surgeries. See, Kingdom T. T., Orlandi R. R., *Image-Guided Surgery of the Sinuses: Current Technology and Applications*, Otolaryngol. Clin. North Am. 37(2):381-400 (April 2004). Generally speaking, in a typical IGS procedure, a digital tomographic scan (e.g., a CT or MRI scan) of the operative field (e.g., the nasal cavities and paranasal sinuses) is obtained prior to surgery. A specially programmed computer is then used to convert the digital tomographic scan data into a digital map. During surgery, sensors mounted on the surgical instruments send data to the computer indicating the position of each surgical instrument. The computer correlates the data received from the instrument-mounted sensors with the digital map that was created from the preoperative tomographic scan. One or more image(s) is/are then displayed on a monitor showing the tomographic scan along with an indicator (e.g., cross hairs or an illuminated dot) of the real time position of each surgical instrument. In this manner, the surgeon is able to view the precise position of each sensor-equipped instrument relative to the surrounding anatomical structures shown on the tomographic scan.

A typical IGS surgery system of the prior art includes a) a computer work station, b) a video monitor, c) one or more surgical instruments having sensors mounted thereon, d) a localizer and e) a sensor tracking system. The sensor(s) mounted on the surgical instruments and the corresponding tracing system may be optical, electromagnetic or electromechanical. The localizer functions to localize or "register" the preoperative tomographic image data with the real time physical positioning of the patient's body during surgery. The sensor tracking system serves to track the position of each sensor equipped surgical instrument during the surgery and to communicate such information to the computer workstation.

In IGS systems that employ optical sensors/tracking systems, optical sensors (e.g., infrared light emitting LEDs) are placed on the surgical instruments and on a localizer frame worn by the patient. A camera is positioned such that it receives light emitted from the sensors. One example of an optical IGS system that is useable in ENT and sinus surgery is the LandmarX Evolution® ENT II Image Guidance System available from Medtronic Xomed Surgical Products, Inc., Jacksonville, Fla.

In IGS systems that employ electromagnetic sensors/tracking systems, radiofrequency electromagnetic sensors (e.g., electromagnetic coils) are placed on the surgical instruments and on a localizer frame worn by the patient. A transmitter is positioned near the operative field. The transmitter transmits signals that are received by the instrument-mounted sensors. The tracking system detects variations in the electromagnetic field caused by the movement of the instrument-mounted sensors relative to the transmitter. Examples of commercially available electromagnetic IGS systems that have been used in ENT and sinus surgery include the ENTrak Plus™ and InstaTrak ENT™ systems available from GE Medical Systems, Salt Lake City, Utah. Other examples of electromagnetic image guidance systems that may be modified for use in accordance with the present invention include but are not limited to those available from Surgical Navigation Technologies, Inc., Louiville, Colo., Biosense-Webster, Inc., Diamond Bar, Calif. and Calypso Medical Technologies, Inc., Seattle, Wash.

In IGS systems that employ electromechanical sensors/tracking systems, a multi-jointed articulating mechanical arm is attached to the surgical instrument and sensors to measure movements of the joints. The computer determines the location of the instrument based on signals received from the sensors. Electromechanical systems have not been widely used in ENT or sinus surgery.

In any IGS system used in sinus surgery or other ENT applications, it is imperative that the localization system provide accurate "registration." Registration is the process of matching two sets of data (i.e., the preoperative tomographic scan data and the intraoperative patient body position data) so that the image displayed on the monitor will accurately show the position(s) of the surgical instrument(s) relative to the locations of anatomical structures shown on the tomographic scan. A number of different registration strategies have been used, including intrinsic strategies as well as extrinsic strategies.

The registration strategy most widely used in sinus surgery and other ENT procedures is an intrinsic registration strategy known as anatomical fiducial registration. A number of fiducial markers are placed at specific anatomical locations on the patient's body during the preoperative tomographic scan and during the surgical procedure. These fiducial markers are typically positioned on the patient's head or face at locations that correspond to specific anatomical landmarks within the ears, nose and/or throat. The fiducial markers may be mounted on a head set or frame that is worn by the patient or the fiducial markers may be affixed directly to the patient's body (e.g., by adhesive attachment to the skin, anchoring into bone, etc.).

Once the registration process has been completed, the sinus surgery or other ENT procedure is performed. To correlate head position with the tracking system, the fiducial markers must remain in fixed position on or in the patient's body until after the surgery has been completed. Unlike neurosurgical procedures that require the patient's head to be fixed in a rigid stereotactic frame, IGS systems that use fiducial markers mounted on or in the patient's body allow for free movement and repositioning of the patient's head during surgery.

When applied to functional endoscopic sinus surgery (FESS) the use of image guidance systems allows the surgeon to achieve more precise movement and positioning of the surgical instruments than can be achieved by viewing through an endoscope alone. This is so because a typical endoscopic image is a spatially limited, 2 dimensional, line-of-sight view. The use of image guidance systems provides a real time, 3 dimensional view of all of the anatomy surrounding the operative field, not just that which is actually visible in the spatially limited, 2 dimensional, direct line-of-sight endoscopic view.

One shortcoming of the prior art IGS systems used in sinus surgery and other ENT procedures is that the sensors have been mounted on proximal portions of the instruments (e.g., on the handpiece of the instrument) such that the sensors remain outside of the patient's body during the surgical procedure. Because these prior art surgical instruments were of rigid, pre-shaped construction, the proximally mounted sensors could be used to accurately indicate to real time position of the distal tip of the instrument. However, in the new FTSI procedures and other new ENT procedures that use flexible and/or malleable catheters and instruments, it is no longer suitable to mount the sensors on proximal portions of the surgical instruments such that the sensors remain outside of the body. Rather, it will be necessary to mount or integrate the sensors at the distal tips of the instruments and/or at other locations on portions of the instruments that are actually inserted into the patient's body, thereby allowing for flexibility or malleability of the instrument shaft.

The present invention provides new sensor-equipped devices that are useable to perform image guided FTSI procedures as well as a variety of other image guided ENT procedures. Additionally, the present invention provides improvements and modifications to the prior art IGS systems and methods to facilitate the performance of image guided FTSI and other image ENT procedures with minimal or less iatrogenic trauma to and/or alteration of anatomical structures that are not involved in the disorder being treated.

SUMMARY OF THE INVENTION

The present invention generally provides methods, systems and devices for performing image guided FTSI procedures as well as other image guided procedures for the treatment of sinusitis and other disorders of the paranasal sinuses, ears, nose and/or throat.

In accordance with the invention, there is provided a method and system for performing an image guided treatment procedure to treat a disease or disorder of an ear, nose, throat or a paranasal sinus in a human or animal subject. In this method and system, a working device (e.g., guidewires, catheters, cannula, tubes, dilators, balloons, substance injectors, needles, penetrators, cutters, debriders, microdebriders, hemostatic devices, cautery devices, cryosurgical devices, heaters, coolers, scopes, endoscopes, light guides, phototherapy devices, drills, rasps, saws, etc.) is inserted into an ear, nose, throat or paranasal sinus of the subject and used to carry out or facilitate at least a portion of the treatment procedure. A sensor is positioned on or in the portion of the working device that becomes inserted into the ear, nose, throat or paranasal sinus of the subject. An image guidance system is used to determine the location of the sensor when the sensor is positioned within an ear, nose, throat or paranasal sinus of the subject, thereby providing a real time indication of the positioning and movement of the working device during the treatment procedure. In some applications, a preoperative tomographic scan (e.g., a CT scan, MRI scan, PET scan, 3 dimensional fluoroscopy such as FluoroCT, etc.) may be obtained and the image guidance system may be programmed to display the tomographic images on a video monitor along with a real time indication (e.g., cross hairs, an illuminated dot, etc.) of the location of the working device relative to the anatomical structures shown on the tomographic image. In some embodiments, an endoscope or intranasal camera may additionally be used to provide a direct line-of-sight video image through the nasal cavity. Such direct line-of-sight video image may be displayed on a separate monitor or may be integrated with the tomographic image data to provide a single monitor display combining 1) the real time line-of-sight video image, 2) indicia (e.g., dotted lines) depicting anatomical structures that are hidden from view on the real time line-of-sight video image and 3) indicia of instrument position provided by the image guidance system. In some applications, the indicia of instrument position may consist of a single indicator (e.g., cross hairs or a dot) indicating the current position of the working device within the subject's body. In other applications, the indicia of instrument position may consist of a series of marks (e.g., a sharp dot followed by a series of phantom dots) indicating the path of prior or future advancement or movement of the working device. Also, in some applications, the working device may optionally include a rotation indicator (e.g., an accelerometer) and the image guidance system may be further programmed to sense and indicate the rotational orientation of the working device within the subject's body.

Further in accordance with the invention, there are provided sensor-equipped working devices (e.g., guidewires, catheters, cannula, tubes, dilators, balloons, substance injectors, needles, penetrators, cutters, debriders, microdebriders, hemostatic devices, cautery devices, cryosurgical devices, heaters, coolers, scopes, endoscopes, light guides, phototherapy devices, drills, rasps, saws, etc.) useable to perform image guided FTSI procedures or other image guided ENT procedures. These image guided working devices of the present invention generally comprise an elongate shaft that is insertable through the nose to a location within a paranasal sinus, ear, nose or throat of the subject and one or more sensor(s) is/are positioned on or in the device at a location that becomes inserted into the subject's body during the procedure. In some embodiments, a sensor may be located at the distal tip of the device. Additionally or alternatively, sensor(s) may be located at other locations on the shaft of the device, such as at the location of a particular working element (e.g., a dilator, balloon, substance injector, needle, penetrator, cutter, debrider, microdebrider, hemostatic device, cautery device, cryosurgical device, heater, cooler, scope, lense, port, endoscope, light guide, phototherapy device, drill, rasp, saw, etc.). In some embodiments, the shaft of the working device proximal to the sensor(s) may be flexible or malleable. Such flexibility or malleability may allow the working device to be advanced though tortuous regions of the intra nasal anatomy and/or to be positioned behind obstructive anatomical structure(s) (e.g., behind the uncinate process) without traumatizing or requiring removal or surgical modification of the obstructive anatomical structure(s).

Still further in accordance with the present invention, there is provided a system of working devices specifically useable to perform an image guided FTSI procedure. Such system generally comprises a flexible guidewire that is advanceable into the ostium of a paranasal sinus and a dilation catheter that is advanceable over the guidewire and useable to dilate the ostium of the paranasal sinus. A sensor is located on a portion of the guidewire and/or dilation catheter that becomes positioned within the subject's body. The sensor communicates with the image guidance system to provide real time indicia of the position of the guidewire and/or dilation catheter such that the operator may precisely position the dilator within the desired sinus ostium without the need for obtaining direct line-of-sight endoscopc view of that sinus ostium. Optionally, the system may additionally comprise a tubular guide through which the guidewire and/or dilation catheter may be advanced. The tubular guide may be rigid, flexible or malleable and may be specifically configured to be advanced through the nose to a position within or near the ostium of the affected paranasal sinus.

Still further in accordance with the present invention, there are provided fiducial marker devices that may be precisely and reproducibly positioned within the mouth of a human subject. In some embodiments, these fiducial marker devices may incorporate brackets, projection of other configurational attributes for mounting of a transmitter useable in conjunction with an electromagnetic image guidance system.

Still further in accordance with the present invention there are provided methods and systems for image guided procedures wherein a single sensor is mounted on a working device that is inserted into the body (e.g., into a paranasal sinus, and a plurality of transmitters are positioned outside of the subject's body such that the device-mounted sensor will receive signals from at least 3 transmitters, thereby enabling a computer within the image guidance system to compute (e.g., triangulate) the three dimensional position of the sensor within the subject's body.

Further aspects, details and embodiments of the present invention will be understood by those of skill in the art upon reading the following detailed description of the invention and the accompanying drawings.

BRIEF DESCRIPTION OF THE DRAWINGS

FIG. 4A is a partial cut away view of a first embodiment of a sensor equipped balloon dilation catheter of the present invention.

FIG. 4B is a cross sectional view through line 4B-4B of FIG. 4A.

FIG. 4C is a partial cut away view of a second embodiment of a sensor equipped balloon dilation catheter of the present invention.

FIG. 4D is a cross sectional view through line 4D-4D of FIG. 4C.

FIG. 4E is a partial cut away view of a third embodiment of a sensor equipped balloon dilation catheter of the present invention.

FIG. 4F is a cross sectional view through line 4F-4F of FIG. 4E.

FIG. 4G is a partial cut away view of a fourth embodiment of a sensor equipped balloon dilation catheter of the present invention.

FIG. 4H is a cross sectional view through line 4H-4H of FIG. 4G.

FIG. 4I is a partial cut away view of a fifth embodiment of a sensor equipped balloon dilation catheter of the present invention.

FIG. 4J is a cross sectional view through line 4J-4J of FIG. 4I.

FIG. 14A is a top perspective view of a first embodiment of a fiducial marker mouthpiece according to the present invention.

FIG. 14B is a side perspective view of the fiducial marker mouthpiece of FIG. 14 A.

FIG. 15A is a top perspective view of a second embodiment of a fiducial marker mouthpiece according to the present invention.

FIG. 15B is a side perspective view of the fiducial marker mouthpiece of FIG. 15 A.

FIG. 15 C is a front view of the mouth of a human subject having the fiducial marker mouthpiece of FIGS. 15A and 15B in its operative position.

DETAILED DESCRIPTION

The following detailed description, the drawings and the above-set-forth Brief Description of the Drawings are intended to describe some, but not necessarily all, examples or embodiments of the invention. The contents of this detailed description, the accompanying drawings and the above-set-forth brief descriptions of the drawings do not limit the scope of the invention or the scope of the following claims, in any way.

In this invention, various types of working devices are equipped with sensors and are used to perform interventional procedures within the paranasal sinuses, ears, noses and throats of human or animal subjects, while an image guidance system is used to track the location of the sensor(s) and, hence, the location(s) of the working device(s). FIGS. 1-6 and 11 show examples of sensor equipped working devices of the present invention. FIGS. 7A-17 show various components and operational aspects of an image guidance system of the present invention and its use in conjunction with the sensor equipped working devices of the present invention.

Figure 1:
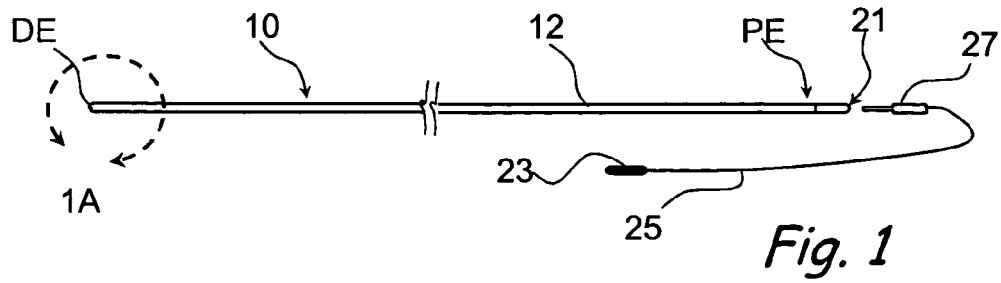
FIG. 1 is a side view of a sensor-equipped guidewire of the present invention.
Figure 1A:
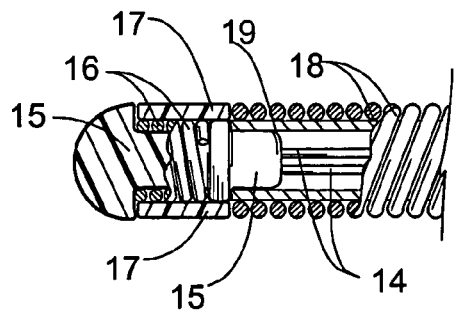
FIG. 1A is an enlarged cut-away view of the distal end of the sensor-equipped guidewire of FIG. 1.
Figure 16:
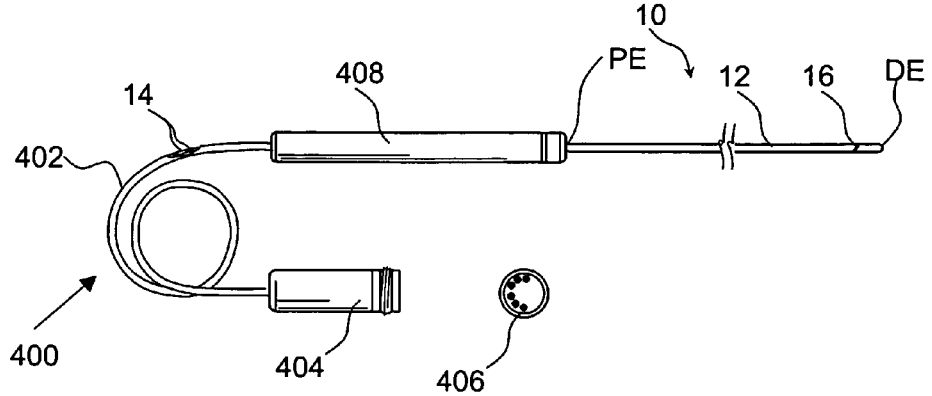
FIG. 16 is a partial cut-away side view of a sensor equipped guidewire of the present invention attached to a cable/connector assembly of the present invention.
Figure 17:
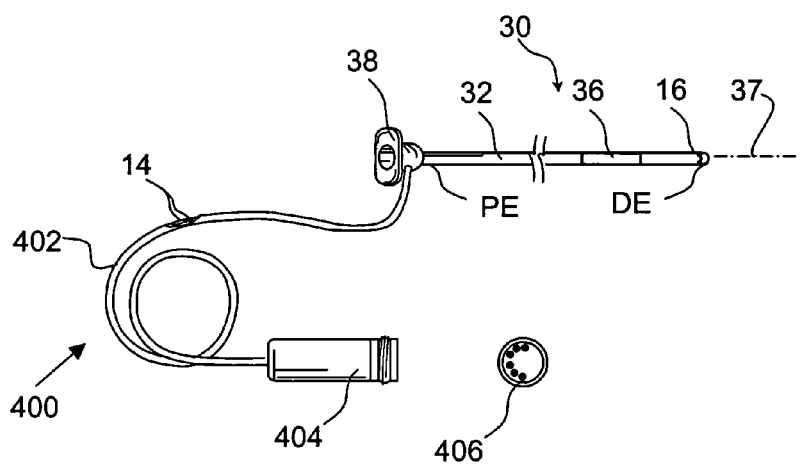
FIG. 17 is a partial cut-away side view of a sensor equipped working device of the present invention having a cable/connector assembly of the present invention attached thereto.

FIGS. 1 and 1A show a sensor equipped guidewire 10 that may be inserted through a nostril (with or without a guide tube or guide catheter) and advanced to a desired location within a paranasal sinus, ear, nose or throat. This sensor-equipped guidewire 10 comprises an elongate flexible body 12 having a proximal end PE and a distal end DE. As shown in the cut-away view of FIG. 1A, the elongate body 12 comprises a core member 19 which may be solid or tubular. In the particular example shown, the core member 19 is tubular and comprises stainless steel hypotube. Optionally, an outer member 18 such as a helical strand or wire may be wound or otherwise disposed about the core member 19, as is well known in the art of guidewire manufacturing. In the particular example shown, a distal tip member 15 formed of electrically insulating material (e.g., plastic) is received within and/or affixed to the distal end of the core member 19 by any appropriate means such as adhesive (e.g., epoxy), mechanical innerlocking, frictional fit, etc. An electromagnetic sensor 16 (e.g., an electromagnetic coil) is disposed (e.g., coiled) about the mid-region of the non-conductive distal tip member 15. Optionally, an electrically insulating cylindrical cover 17 (e.g. a plastic sheath, plastic shrink wrap, etc) may be disposed about the electromagnetic sensor 16. The outer surface of such cover 17, if present, may be substantially flush with the adjacent outer surface of the outer member 18, if present, as shown in FIG. 1A. In embodiments where the come member 19 is hollow (e.g., hypotube) sensor leads 14 may extend from the electromagnetic sensor coil 16, through the lumen of the core member 19 and to or out of the proximal end PE of the guidewire 10. In some embodiments, a connector 21 (e.g., a jack) located on the proximal end PE of the guidewire 10 may be configured to connect to a corresponding connector 27 (e.g., a plug) located on one end of a cable 25. A connector 23 on the other end of the cable 25 is then connectable to an image guidance system that is programmed for use in combination with such guidewire, as described more fully herebelow. In some embodiments, the guidewire's proximal connector 21 may be connected to another types of cable/connector assembly 400 as shown in FIGS. 16 and 17 and described herebelow. Also, in some embodiments of devices of this invention, the sensor 16 may be in wireless communication with an an image guidance system, as explained more fully hereblow.

It will also be appreciated that the outer helical wire wrap 18 may formed of wire, a plastic strand, a helically cut metal or plastic tube, or any other suitable material. It will also be appreciated that the guidewire 10 may be constructed such that at least a distal portion of the outer member 18 or other outer material (e.g., helically cut tube) may be made of substantially nonferromagnetic material and may extend over the sensor 16 such that the sensor is disposed within a substantially nonferromagnetic portion of the outer member 18. The sensor leads 14 may then extend through the outer member 18.

Furthermore, it is to be appreciated that, in this guidewire 10 or any other sensor equipped device of the present invention, the sensor 16 need not necessarily be longitudinally aligned with or disposed about the longitudinal axis of the device. Rather, the sensor may be disposed transversely within the device or in any other suitable attitude, position or alignment. For example, in a guidewire, catheter or other device that has a lumen or cavity formed therein, a crossmember may extend transversely across such lumen or cavity and the sensor 16 may be disposed about such crossmember (e.g., an electromagnetic coil may be wound about the cross member). Such construction may allow for better selectivity and control of the magnetic permeability of the material lying under and/or over the sensor 16 and may allow for a more robust design and construction of certain devices.

Examples of commercially available image guidance systems that may be modified and programmed for use in connection with this sensor equipped guidewire 10, as well as the other sensor equipped working devices described in this patent application, include the ENTrak Plus™ and InstaTrak ENT™ systems available from GE Medical Systems, Salt Lake City, Utah as well as systems available from Surgical Navigation Technologies, Inc., Louisville, Colo., Biosense-Webster, Inc., Diamond Bar, Calif. and Calypso Medical Technologies, Inc., Seattle, Wash.

As described herebelow, it will often be desirable to advance catheters or other devices over the guidewire 10 after the guidewire 10 has been inserted into the subject's body. Thus, the guidewire body 12 and any proximal connector 21 may be small enough in diameter to allow the desired catheter(s) and/or other devices(s) to be advanced over the guidewire body 12 and any proximal connector 21.

Figure 2A:
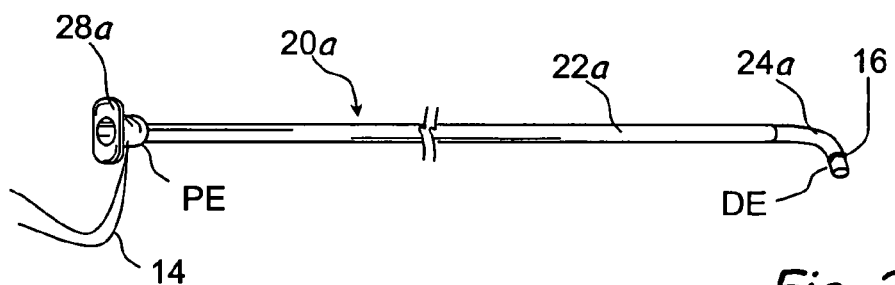
FIG. 2A is a perspective view of a sensor-equipped guide tube of the present invention.
Figure 2B:
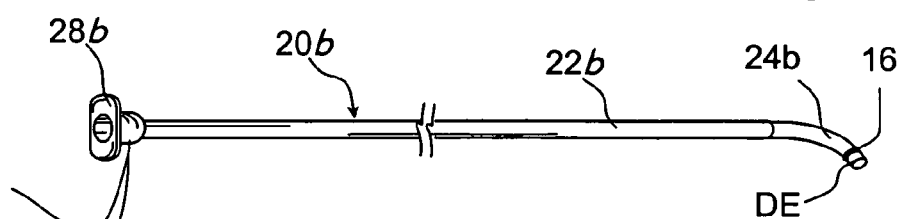
FIG. 2B is a perspective view of another sensor-equipped guide tube of the present invention.

FIGS. 2A and 2B show examples of sensor equipped tubular guides 20a, 20b that may be inserted through a nostril (with or without a guidewire) and advanced to a desired location within a paranasal sinus, ear, nose or throat. All of portions of tubular guides of the present invention may be rigid, flexible or malleable. In the particular examples shown in FIGS. 2A and 2B, the tubular guides 20a, 20b are substantially rigid and preformed to a specific shape to facilitate advancement of the tubular guide 20a or 20b to locations that are immediately adjacent to the ostia of paranasal sinuses such that working devices such as dilation catheters and the like may be advanced through the tubular guide 20a or 20b and into or through the adjacent sinus ostium.

Specifically, FIG. 2A shows an example of a tubular guide 20a that is configured for use in accessing the ostium of a maxillary sinus of a human subject. This tubular guide 20a comprises a substantially straight proximal portion 22a and a curved distal portion 24a. A Luer hub 28a is mounted on the proximal end PE of the proximal portion 20a. A sensor 16, such as an n electromagnetic sensor coil, is positioned on the curved distal portion 24a. Wire leads 14 may extend from the electromagnetic sensor coil 16, though the proximal portion 22a and out of the proximal end PE of the tubular guide 20a, as shown, for attachment of the tubular guide 20a to an image guidance system that is programmed for use in combination with such guidewire as described more fully herebelow. Although various types of construction and materials may be used, in this particular example, the proximal portion 22a comprises stainless steel hypotube of approximately 0.040 inch to approximately 0.200 inch outer diameter. It will be appreciated that in embodiments where stainless steel or other metal is used, such metal will be separated from the sensor 16 by insulating material(s) and/or sufficient distance to avoid any affect that the meal may have on the accuracy or function of the sensor 16. A plastic tube formed of rigid plastic (e.g., pebax, polyurethane, etc) is advanced through the lumen of the hypotube such that a portion of the plastic tube protrudes out of and beyond the distal end of the hypotube. This protruding portion of the plastic tube is then plastically deformed (e.g., thermally formed) to the desired curvature, thereby forming the curved distal portion 24a of the tubular guide 20a. In this example, the sensor 16 comprises a coil that is wound about or positioned about the outer surface of the curved distal portion 24a of the tube. Optionally, a plastic film or other electrically insulating cover (e.g, an outer skin) may be heat shrunk or otherwise disposed and secured about the electromagnetic sensor 16 to provide a smooth outer surface in the area where the electromagnetic sensor 16 is mounted. The electromagnetic sensor 16 may be mounted at or near the distal tip of the tubular guide 20a to permit the associated image guidance system to monitor the real time position of the distal tip of the guide 20a. Wire leads 14 may extend from the electromagnetic sensor 16, through or along the distal portion 24a, through or along the proximal portion and out of the proximal end PE of the tubular guide 20a, as shown. In this regard, the plastic tube that extends through the metal hypotube and protrudes therefrom to form the curved distal portion 14a may have a large working lumen as well as one or two additional lumens through which the wire leads 14 may pass. Alternatively, the wire leads 14 may pass along the outer surface of the distal portion 24a, the through the lumen of the hupotube, between the outer surface of the inner plastic tube and inner surface of the outer hypotube. In this particular example, the distal portion 24a is substantially rigid and is preformed to a curve of from approximately 70 degrees through approximately 135 degrees, so as to be useable for accessing the ostium of a maxillary sinus without requiring substantial cutting or surgical modification of the uncinate process or other normal anatomical structures within the nose. Alternatively, it will be appreciated that the distal portion 24a may be malleable (e.g., a malleable metal, polymer or metal-polymer composite) so that the operator may shape the distal portion 24a as desired, depending on the particular sinus ostium or other location to be accessed, anatomical irregularities of the subject, etc. So long as the electromagnetic sensor coil 16 is located distal to any curve(s) introduced in the malleable distal segment, the introduction of such custom made curve(s) will not require any recalibration or otherwise hamper the ability of the image guidance system to sense the position of the distal end of the tubular guide 20a. In operation, this tubular guide 20a is inserted through the subject's nostril, either alone, over a previously inserted guidewire or with a guidewire pre-inserted into the lumen of the tubular guide 20a. The tubular guide 20a is then advanced through the medial meatus and rotated to cause the curve of the distal portion 24a to pass over the uncinate process such that the open distal end DE of the tubular guide 20a is positioned adjacent to and in substantial alignment with the ostium of the maxillary sinus.

The tubular guide 20b shown in FIG. 2B may be constructed and used in the same manner as the tubular guide 20a of FIG. 2A except that the curved distal portion 24b has a less severe curvature than the distal portion of the 24a of the guide shown in FIG. 2A. In this particular example, the distal portion 24b is substantially rigid and is preformed to a curve of from approximately 30 degrees through approximately 90 degrees, thereby being useable for accessing the ostia of frontal sinuses.

Figure 3:
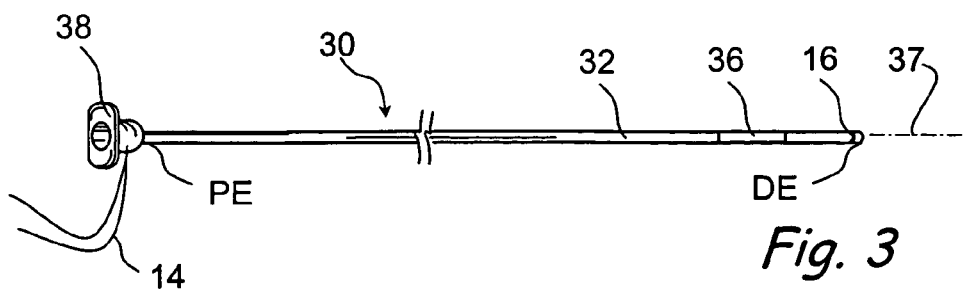
FIG. 3 is a schematic perspective view of a sensor-equipped working device useable to perform a therapeutic or diagnostic procedure within an ear, nose, throat or paranasal sinus.

It is to be appreciated that the particular curvatures and shapes of the tubular guides 20a, 20b shown in FIGS. 2A and 2B are merely examples of the many shapes and configurations in which tubular guides of the present invention may be configured to accesses specific locations within the nose, paranasal sinuses, Eustacian tubes, etc. Additionally, it is to be appreciated that any of the guidewires 10, tubular guides 20a, 20b or other working devices 30 of this invention may be steerable, bendable, malleable or capable of being articulated. FIG. 3 shows a generic example of a sensor-equipped working device 30 of the present invention. This device 30 comprises an elongate shaft 32, a sensor 16, a working element 36 and wires 14 that extend from the sensor 16 through the shaft 32 and out of the proximal end PE of the device 30. In some embodiments, the outer diameter of the working device 30 may be less than the inner diameter of a sensor-equipped tubular guide 20a or 20b or other tubular guide such that the working device 30 may be advanced through a tubular guide to a desired location where treatment is to be applied. Additionally or alternatively, the working device 30 may have a guidewire lumen extending through or adjacent to the shaft 32 such that the working device 30 may be advanced over a sensor-equipped guidewire 10 or other guide member to a desired location where the treatment is to be applied. In this example, the sensor 16 comprises a coil that is wound about or positioned about the outer surface of shaft 32 a known distance from the distal end DE of the device 30. Provided that any bending, curving or flexing of the shaft 32 occurs proximal to the sensor 16, the spatial relationship of the sensor 16 to the distal end DE will remain constant and, thus, the position of the distal end DE of the device 30 may be determined and displayed on a video screen on the basis of the sensed location of the sensor 16. In some embodiments, one or more sensors may be positioned in known spatial relation to the working element so as to provide the ability to determine and display the real time location of the working element on the basis of the sensed location of the sensor(s) 16. In embodiments where the sensor comprises a wire coil, such coil may be positioned within or wound about the outer surface of the elongate shaft 32. Optionally, a plastic film or other electrically insulating cover (e.g, an outer skin) may be heat shrunk or otherwise disposed and secured about the sensor 16 to provide a smooth outer surface in the area where the sensor 16 is mounted. Wire leads 14 may extend from the sensor 16, through the shaft 32 to facilitate connection of the sensor 16 to an image guidance console (e.g., a computer workstation) as described herein. Alternatively, the wire leads 14 may pass along the outer surface of the shaft 32 and may be secured by adhesive, a surrounding wrap, sheath or skin, etc. These wire leads 14 or the sensor 16 itself may be connected directly, indirectly through an intervening apparatus (e.g., a cable, self-calibrating instrument system or other intervening apparatus) or by wireless connection to the console 76 and/or computer 78. In applications where the sensor 16 or its leeds 14 are connected to the console 76 and/or computer 78 by way of a self-calibrating instrument system, such self-calibrating instrument system may comprise a sensor-equipped distal instrument attached to a proximal handpiece. The instrument system would be initially calibrated by touching the sensor-equipped distal instrument to fiducial markers. Once the instrument system was calibrated, the sensor-equipped distal instrument could be exchanged for other sensor-equipped distal instruments without requiring the user to recalibrate the instrument system. Instead, the instrument system would self calibrate by means of the proximal handpiece reading calibration information embedded electronically in a tag on the distal instrument.

The working element 36 may be positioned at a location between the proximal end PE and distal end DE, as shown in the example of FIG. 3. Alternatively, the working element 36 may be positioned at or on the distal end DE of the device 30, depending on the mode of action and intended use of the working element. The working element 36 may perform or facilitate any type of therapeutic or diagnostic function. Examples of working elements 36 that may be used include but are not limited to: dilators, balloons, substance injectors, needles, penetrators, cutters, debriders, microdebriders, hemostatic devices, cautery devices, cryosurgical devices, heaters, coolers, scopes, lenses, ports, endoscopes, light guides, phototherapy devices, drills, rasps, saws, etc. Some specific examples of working elements 36 and their uses in ENT procedures are described in U.S. patent application Ser. No. 10/829,917 entitled "Devices, Systems and Methods for Diagnosing and Treating Sinusitis and Other Disorders of the Ears, Nose and/or Throat," Ser. No. 10/912,578 entitled "Implantable Device and Methods for Delivering Drugs and Other Substances to Treat Sinusitis and Other Disorders," Ser. No. 10/944,270 entitled "Apparatus and Methods for Dilating and Modifying Ostia of Paranasal Sinuses and Other Intranasal or Paranasal Structures" and Ser. No. 11/037,548 entitled "Devices, Systems and Methods For Treating Disorders of the Ear, Nose and Throat," which are expressly incorporated herein by reference.

Optionally, any working device 30 of this invention, may include a guide member 37, such as a flexible, malleable or rigid wire or other elongate member, that extends from the distal end DE of the device, as shown in phantom in FIG. 3. This guide member 37 may be tapered or nontapered. The guide member 37 will typically be smaller in diameter than the body 32 of the working device 30 such that the guide member may be easily advanced through an ostium of other anatomical opening, thereby facilitating or "guiding" placement of the body 32 of the device 30 in a position adjacent to that ostium or opening and/or thereby facilitating or guiding further advancement of the body 32 of the device 30 through that ostium or opening.

Figure 4:
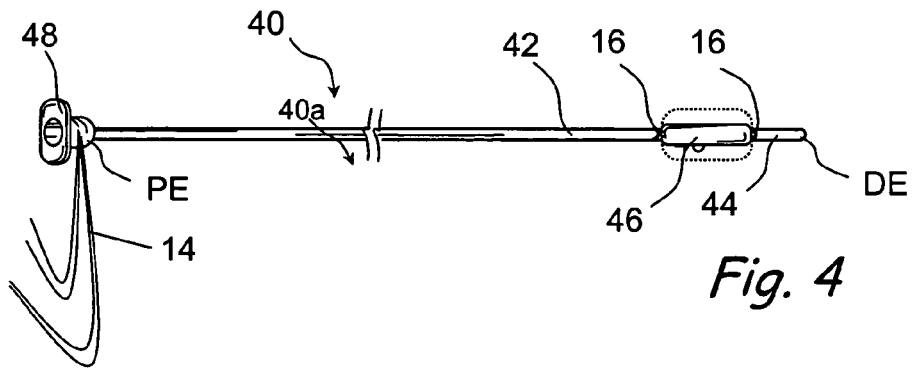
FIG. 4 is a perspective view of a sensor-equipped dilation catheter of the present invention.
Figure 4:
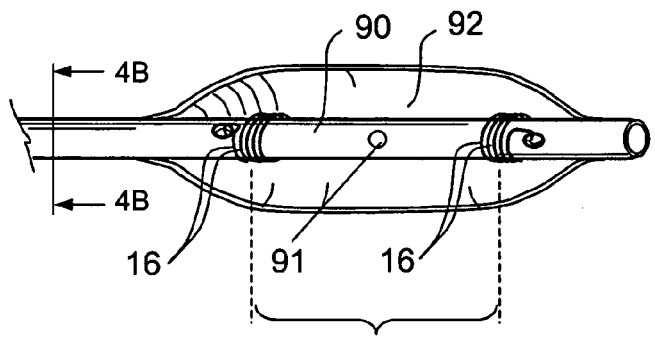
Figure 4:
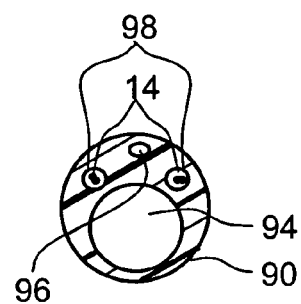
Figure 4:
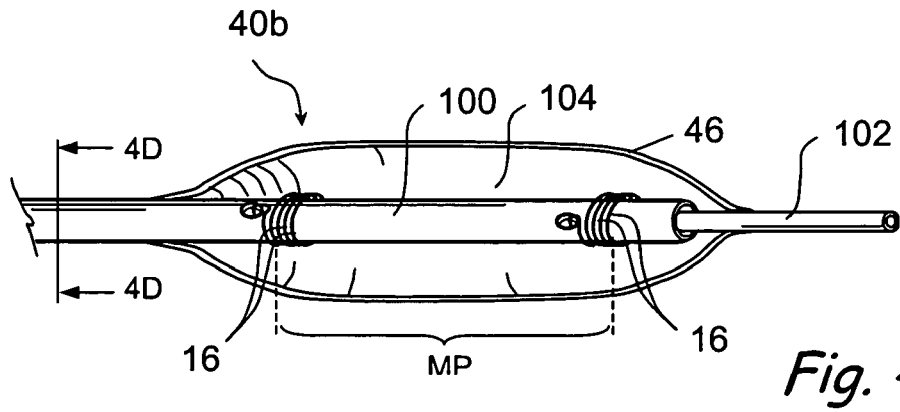
Figure 4:
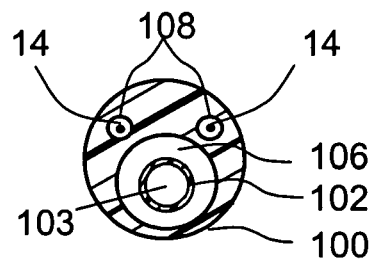
Figure 4:
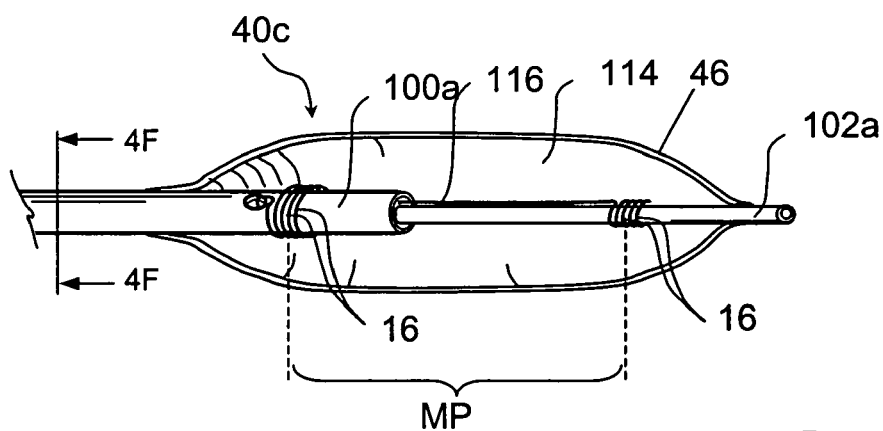
Figure 4:
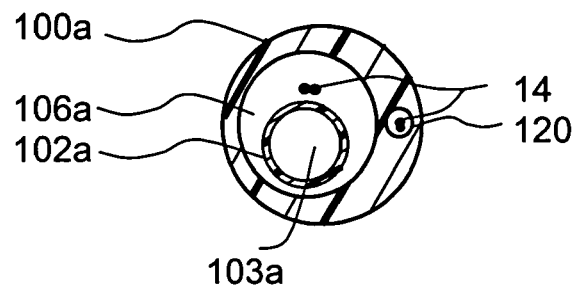
Figure 4:
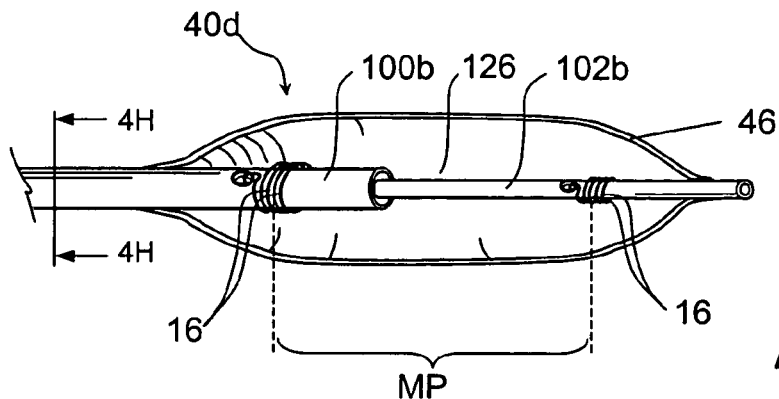
Figure 4:
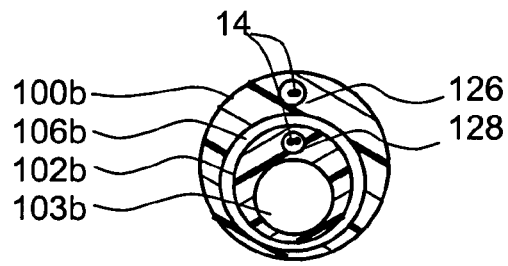
Figure 4:
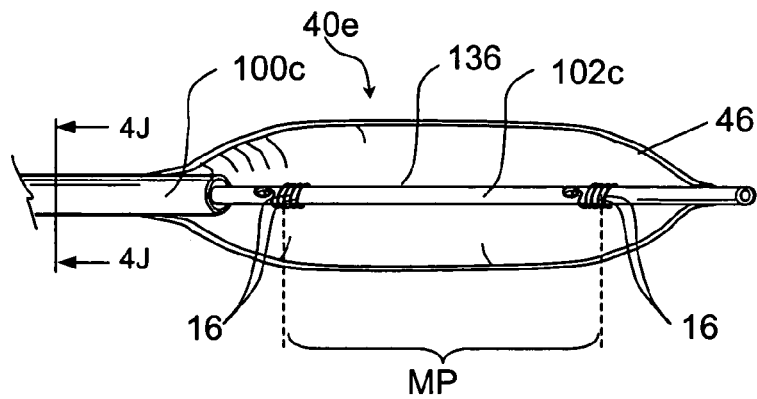
Figure 4:
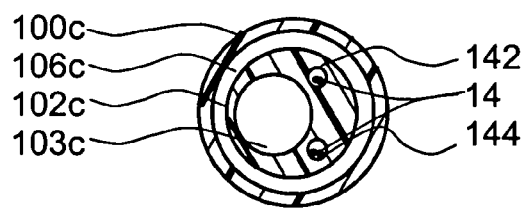

In systems used to perform FTSI procedures, a working device 30 wherein the working element 36 comprises a balloon or other dilator will be used to dilate the ostium of a paranasal sinus. FIGS. 4-4J show some specific examples of sensor equipped working devices in the nature of dilation catheters (e.g., balloon catheters) for dilation of the ostia of paranasal sinuses or other anatomical or pathological structures.

FIGS. 4-4B show an embodiment of a sensor equipped dilation catheter 40*a* comprising a shaft 42 comprising a single, multi-lumen tube, a proximal Luer hub 48, a balloon 46, sensor(s) 16 and sensor leads 14. While any number of sensors 16 may be used, the example shown in FIGS. 4-4B incorporates two (2) sensors 16, wherein one sensor 16 is located near the proximal end of the balloon 46 and the other sensor 16 is located near the distal end of the balloon 46. A through lumen 94 extends from the bore of the proximal Luer hub 48, through the shaft 42 and terminates distally in a distal end opening. This through lumen 94 may be used for fluid infusion/aspiration and/or for guidewire passage. Lead lumens 98 also extend through the shaft 42 and the sensor leads 14 extend through such lead lumens 98. An inflation/deflation lumen 96 extends from a sidearm port 49 on the proximal hub 48, through the shaft 42 and terminates in an aperture 91 within the balloon 46 to facilitate inflation and deflation of the balloon 46. For applications intended to dilate the ostia of paranasal sinuses, the balloon will typically be formed of a relatively non-compliant material such as polyethylene teraphthalate (PET) or nylon of a thickness and density that renders the balloon capable of withstanding inflation pressures of up to approximately 25 atmospheres. The balloon 46 may have a straight cylindrical side wall with tapered ends, as shown, and if the balloon 46 is so constructed, the sensors 16 may be positioned directly beneath the proximal and distal ends of the straight cylindrical midportion MP of the balloon 46 as seen in FIG. 4A. As explained more fully herebelow, this catheter 40 may be advanced to a position where the deflated balloon 46 is positioned within a stenotic ostium of a paranasal sinus with the distal sensor 16 on one side of the ostium and the proximal sensor 16 on the other side of the ostium. The balloon 46 may then be inflated one or more times to desired pressure(s) (e.g., typically pressures ranging from about 10 atmospheres through about 25 atmospheres) to dilate the stenotic ostium. Thereafter, the balloon 46 may be deflated and the dilation catheter 40 removed. FIGS. 4C and 4D show another way in which a sensor equipped dilation catheter 40*b* may be constructed. In this example, the catheter 40*b* differs from that shown in FIGS. 4-4B because its shaft 104 comprises an outer tube 100 and an inner tube 102. The inner tube 102 extends through the outer tube 100 and protrudes out of the distal end of the outer tube 100 by a fixed distance. The sensors 16 are mounted on the outer tube 100 at spaced apart locations such that one sensor 16 is directly beneath the proximal end of the straight walled midportion MP of the balloon 46 and the other sensor 16 is directly beneath the distal end of the straight walled midportion MP of the balloon 46. The outer tube 100 has a main through lumen 106 and two lead lumens 108 through which the sensor leads 14 extend. The inner tube 102 has a through lumen 103 which may be used as a guidewire lumen and/or an infusion/aspiration lumen or for other purposes. The outer diameter of the inner tube 102 is smaller than the inner diameter of the outer tube 100 such that a space exists to allow balloon inflation fluid to be infused into or removed from the balloon 46 through the lumen of the outer tube 100. This embodiment of the dilation catheter 40 shown in FIGS. 4C-4D may be positioned and used to dilate the ostium of a paranasal sinus in the same manner as that described above with respect to the embodiment of FIGS. 4-4B.

FIGS. 4E and 4F show yet another way in which a sensor equipped dilation catheter 40*c* may be constructed. In this example, like the example shown in FIGS. 4C and 4D, the catheter 40*c* has a shaft 114 that comprises an outer tube 100*a* and an inner tube 102*a*, wherein the outer tube 100*a* terminates near the longitudinal midpoint of the balloon 46 and the inner tube 102*a* extends through the outer tube 100*a* and protrudes out of the distal end of the outer tube 100*a* by a fixed distance. In this embodiment of the catheter 40*c*, the proximal sensor 16 is positioned on the outer tube 100*a* at a location that is directly beneath the proximal end of the straight walled midportion MP of the balloon 46 and the other sensor 16 is positioned on the inner tube 102*a* at a location that is directly beneath the distal end of the straight walled midportion MP of the balloon 46. The outer tube 100*a* has a main through lumen 106*a* and one lead lumen 120 through which the sensor leads 14 from the proximal sensor 16 extend. The inner tube 102*a* has a through lumen 103*a* which may be used as a guidewire lumen and/or an infusion/aspiration lumen. The outer diameter of the inner tube 102*a* is smaller than the inner diameter of the lumen 106*a* of outer tube 100*a* such that a space exists to allow balloon inflation fluid to be infused into or removed from the balloon 46 through the lumen 106*a* of outer tube 100*a*.

In the example of FIGS. 4E and 4F, the sensor leads 14 from the distal sensor 16 extend along the outer surface of the inner tube 102*a*, as shown, and may be secured to the outer surface of the inner tube 102*a* by any suitable means such as adhesive, clips, bands, sheathing, shrink wrapping, etc. It is to be appreciated, however, that in any of the embodiments, any of the sensor leads 14 may extend outside of, within or through a lumen of any portion of the catheter shaft, as may be desirable or expedient for manufacturing or operative purposes and/or to minimize electrical interference and optimize signal transmission. For example, FIGS. 4G and 4H show another way in which a sensor equipped dilation catheter 40*d* may be constructed. In this example, like the example shown in FIGS. 4E and 4F, the catheter 40*d* has a shaft 126 that comprises an outer tube 100*b* and an inner tube 102*b*. The outer tube 100*b* terminates near the longitudinal midpoint of the balloon 46 and the inner tube 102*b* extends through the outer tube 100*b* and protrudes out of the distal end of the outer tube 100*b* by a fixed distance. Again, in this embodiment of the catheter 40*d*, the proximal sensor 16 is positioned on the outer tube 100*b* at a location that is directly beneath the proximal end of the straight walled midportion MP of the balloon 46 and the other sensor 16 is positioned on the inner tube 102*b* at a location that is directly beneath the distal end of the straight walled midportion MP of the balloon 46. The outer tube 100*b* has a main through lumen 106*b* and one lead lumen 126 through which the sensor leads 14 from the proximal sensor 16 extend. The inner tube 102*b* has a through lumen 103b which may be used as a guidewire lumen and/or an infusion/aspiration lumen. The outer diameter of the inner tube 102b is smaller than the inner diameter of the outer tube 100b such that a space exists to allow balloon inflation fluid to be infused into or removed from the balloon 46 through the lumen 106b of the outer tube 100b. In this embodiment, a second lead lumen 128 is formed in the wall of the inner tube 102b and the wire leads 14 from the distal sensor 16 extend through such second lead lumen 128, as shown.

FIGS. 4I and 4J show yet another way in which a sensor equipped dilation catheter 40e may be constructed. In this catheter 40e, the shaft 136 comprises an outer tube 100c that terminates within the proximal region of the balloon 46 and the inner tube 102c extends through the outer tube 100c such that it protrudes out of the distal end of the outer tube 100c by a fixed distance. In this embodiment, both the proximal and distal sensors 16 are positioned on the inner tube 102c. Specifically, the proximal sensor 16 is positioned on the inner tube 100c at a location that is directly beneath the proximal end of the straight walled midportion MP of the balloon 46 and a distal sensor 16 is positioned on the inner tube 102c at a location that is directly beneath the distal end of the straight walled midportion MP of the balloon 46. The outer tube 100c has a main through lumen 106c through which the inner tube 102c extends. The inner tube 102c has a through lumen 103c which may be used as a guidewire lumen and/or an infusion/aspiration lumen and two lead lumens 142, 144 through which the sensor leads 14 from the proximal and distal sensors 16 extend. The outer diameter of the inner tube 102c is smaller than the inner diameter of the lumen 106c of outer tube 100c such that a space exists to allow balloon inflation fluid to be infused into or removed from the balloon 46 through the lumen 106c of outer tube 100c.

Although the balloons 46 shown in FIGS. 4-4J are straight walled cylindrical balloons having tapered ends, it is to be appreciated that various other shapes and configurations of balloons may be employed in any embodiments of the dilation catheter 40. For example, one or more depressions or indentations (e.g., an annular depression or groove) may be formed in the midportion MP of each balloon to facilitate positioning of the balloon and seating of ostial tissue or other anatomical tissue within such depressions or indentations. Examples of balloons having such depressions or indentations are described in U.S. patent application Ser. Nos. 10/829,917, 10/944,270 and 11/037,548, which are expressly incorporated herein by reference.

It is to be appreciated that the specific examples shown in the draings are merely examples. Indeed, the sensors 16 may be positioned at many other locations other than those shown in these examples. For example, in any sensor equipped dilation catheter 40, sensor(s) may be located in the center of the balloon 46 or other working element and/or elsewhere on or in the catheter shaft within the balloon 46 or other working element and/or distal to the balloon 46 or other working element and/or proximal to the balloon 46 or other dilator and/or within the wall(s) of the balloon 46 or other dilator.

Also, in any of the working devices having lumen(s) the shaft of the device (e.g., the catheter body) need not be of coaxial (e.g., tube within a tube) design, but alternatively may be a single catheter body having a plurality of lumens. For example, in the case of a balloon dilation catheter, a catheter shaft having four lumens may be used. One lumen may serve as a guidewire/working lumen, one lumen may serve as a balloon 46 inflation/deflation lumen and the other two lumens may serve as passageways for the sensor leads 14. Also, as stated, in any of the sensor equipped devices 10, 20, 30, 40 a fixed guide tip and/or sensor 16 may be located at the distal end DE of the device.

Also, in any embodiment of a sensor equipped dilation catheter 40, the balloon 46 may be replaced by other types of dilators or expandable structures, such as expandable mesh cages and the like.

Also, in any embodiment of a sensor equipped dilation catheter 40, the balloon 46 or other dilator may be coated, textured, equipped with injection ports or otherwise equipped and/or constructed to deliver additional treatment(s) in addition to the primary anatomical dilation. For example, the balloon 46 may be coated with or may comprise a drug or any other substance (e.g., a hemostatic agent or a substance that deters scarring or adhesion formation) that will transfer onto or into the tissue contacted by the balloon. Examples of balloons having such additional treatment delivering capabilities are described in U.S. patent application Ser. Nos. 10/912,578 and 11/037,548, which are expressly incorporated herein by reference.

Additionally, in some embodiments of sensor equipped dilation catheter 40, a stent or other radially expandable implantable device may be mounted on the exterior of the balloon 46 or other dilator such that, when the balloon 46 is inflated (or when any other type of dilator is expanded) the stent or other radially expandable implantable device will be expanded and will remain within the body after the balloon has been deflated (or the other type of dilator contracted) and the dilation catheter 40 removed. Examples of stents and other radially expandable implantable devices that may be used in conjunction with these sensor equipped dilation catheters 40 are described in U.S. patent application Ser. Nos. 10/829,917; 10/912,578; 10/944,270 and 11/037,548, which are expressly incorporated herein by reference.

Figure 5:
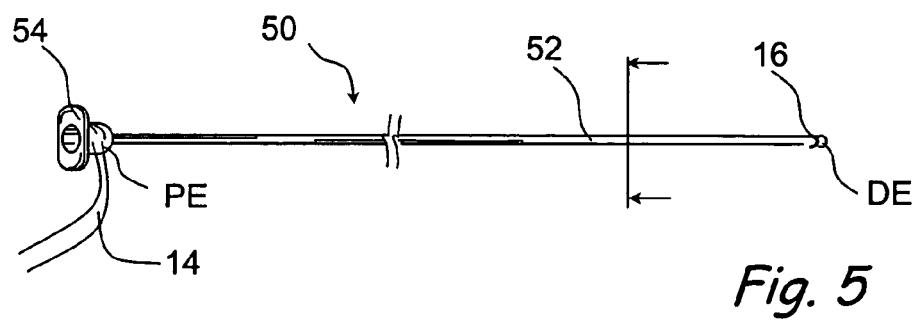
FIG. 5 is a perspective view of a sensor-equipped sub-selective sheath of the present invention.
Figure 5A:
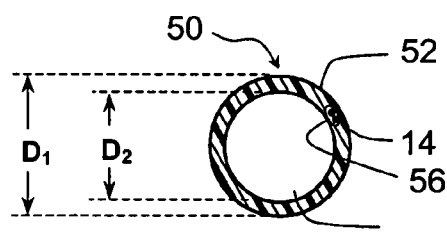
FIG. 5A is a cross sectional view through line 5A-5A of FIG. 5.

In some applications, it may be desirable to utilize a sensor equipped subselective sheath 50, such as that shown in FIGS. 5 and 5A. The sheath 50 shown in FIGS. 5 and 5A comprises an elongate tubular body 52 having a Luer hub 54 on its proximal end PE and a sensor 16, such as an electromagnetic coil located at some desired location, such as at or near the distal end DE of the tubular body 52. A main lumen 216 extends through the tubular body 52 in communication and direct alignment with the bore of the Luer hub 54. A separate lead lumen 56 also extends through the tubular body 52. Sensor lead wires 14 extend through such lead lumen 56 and out of the proximal hub 54 such that the lead wires 14 may be connected to the computer of an image guidance system as described more fully herebelow. In some embodiments, the inner diameter D1 of the sheath lumen 216 will be large enough to allow a guidewire 10 and/or working device 30, 40, 60 to be advanced through the lumen 216 of the subselective sheath 50 and/or the outer diameter D2 of the tubular body 52 will be small enough to advance through a tubular guide 20a, 20b. The tubular body 52 of the subselective sheath 50 may be formed of a polymer such as Pebax, polyimide, high density polyethylene (HDPE), low density polyethylene (LDPE), blends of HDPE/LDPE, etc. and may have a wall thickness from approximately 0.001 inches through approximately 0.050 inches. In some embodiments, a lubricious liner or coating may be disposed within the main lumen 216 to facilitate sliding of guidewires or working devices therethrough.

Figure 6:
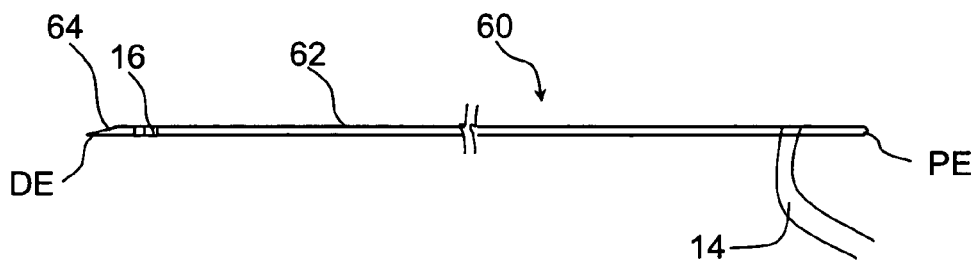
FIG. 6 is a side view of a sensor equipped penetrator of the present invention.

Another type of sensor equipped working device of the present invention is a penetrator 60, as shown in FIG. 6. In the example shown, the penetrator 60 comprises a solid or hollow elongate body 62 (e.g., a plastic or stainless steel rod or hypotube of approximately 14 gage through approximately 27 gage having a sharp tip 64 at its distal end DE. A sensor 16, such as an electromagnetc coil, is positioned at a desired location on the penetrator, such as at or near its distal end DE. In some embodiments a sensor coil may be wrapped about the elongate body 62. A notch or depression may be formed in the elongate body to accommodate such coil wrap and a covering, such as a plastic coating, sleeve, shrink wrap, etc. may be disposed about the coil, thereby providing a smooth outer surface and deterring direct contact of the sensor coil with body fluids or tissues. Sensor lead wires 14 extend through the elongate body 62 exiting near its proximal end PE such that they may be connected to the computer of an image guidance system as described more fully herebelow.

Any of the sensor equipped working devices (e.g., guidewires, catheters, cannula, tubes, dilators, balloons, substance injectos, needles, penetrators, cutters, debriders, microdebriders, hemostatic devices, cautery devices, cryosurgical devices, heaters, coolers, scopes, endoscopes, light guides, phototherapy devices, drills, rasps, saws, etc.) may incorporate biocompatible outer layers or coatings of lubricious material to facilitate smooth advancement of the device through the nasal anatomy, unless the inclusion of such coating would render the device unusable for its intended purpose.

Also, any of the sensor equipped working devices may incorporate a vibrator or other movement imparting apparatus to cause vibration, reciprocation, vacillation or other movement of the working device to facilitate passage of the working device through tight or tortuous anatomical passages, unless the inclusion of such vibrator or other movement imparting apparatus would render the device unusable for its intended purpose.

Figure 7:
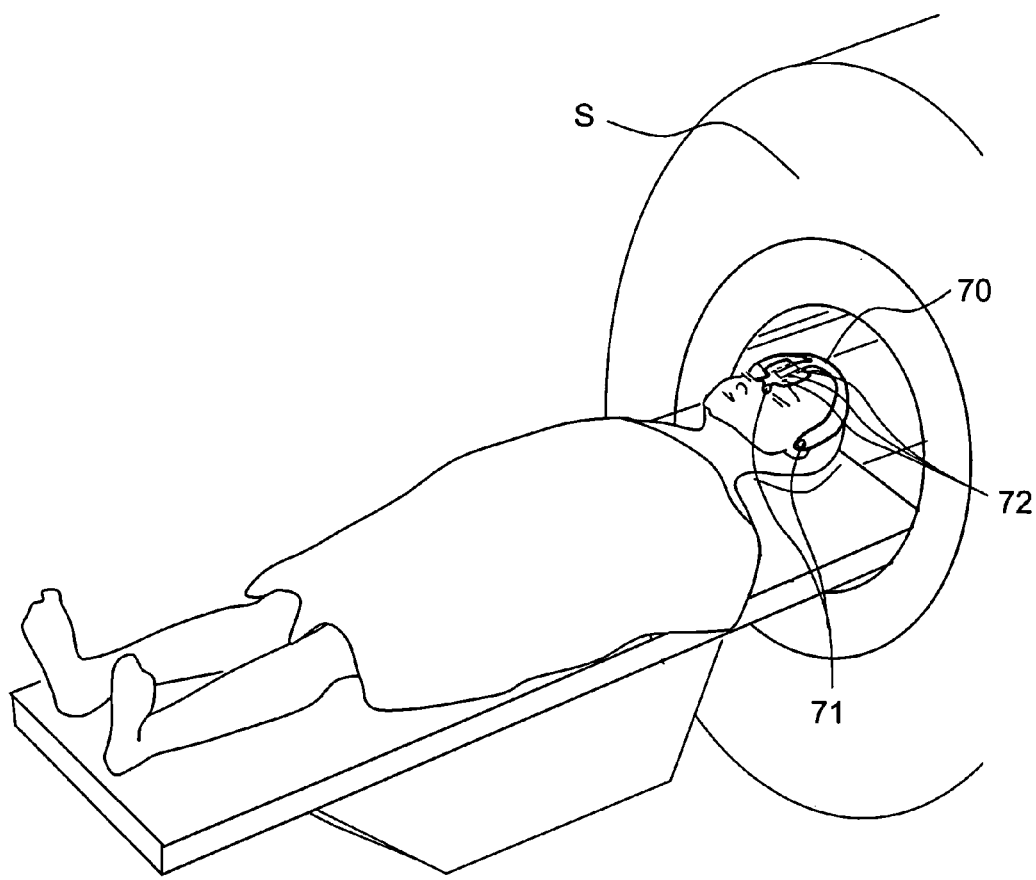
FIG. 7A shows a human subject undergoing a preoperative tomographic scan while wearing a head frame having fiducial anatomical markers thereon.
FIG. 7B is a schematic showing of data from the preoperative tomographic scan being loaded into the computer workstation of the image guidance system in accordance with this invention.
FIG. 7C shows an example of the image guidance system being used to provide a single image display (which may or may not incorporate superimposed data or indicia from multiple sources).
FIG. 7D an example of the image guidance system being used to provide separate displays of multiple images.
FIG. 7E shows the human subject positioned on the operating table and wearing the head frame having fiducial anatomical markers and a transmitter thereon.
Figure 7:
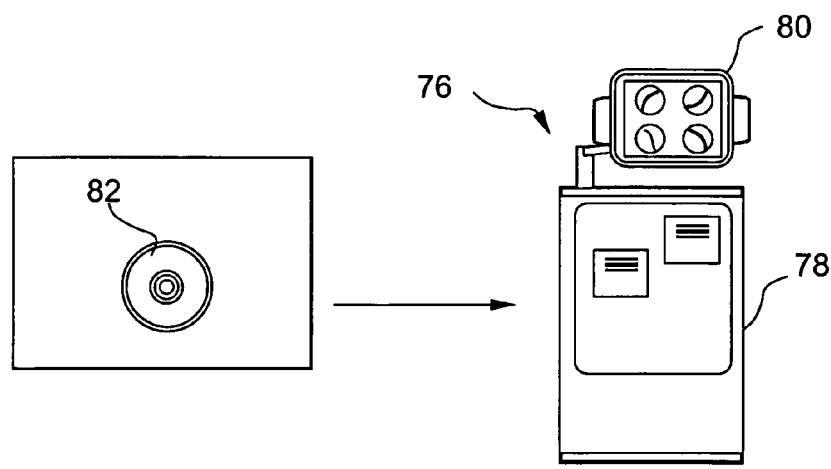
Figure 8:
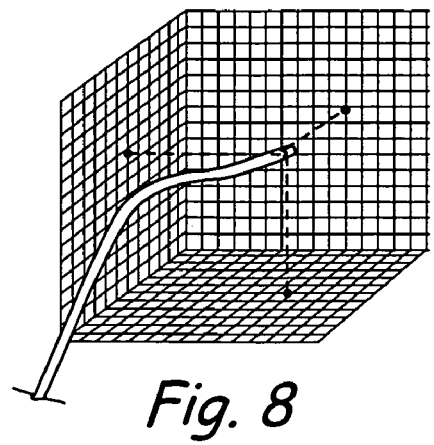
FIG. 8 is a schematic depiction of an electromagnetic field having a sensor equipped working device of the present invention positioned therein.
Figure 9:
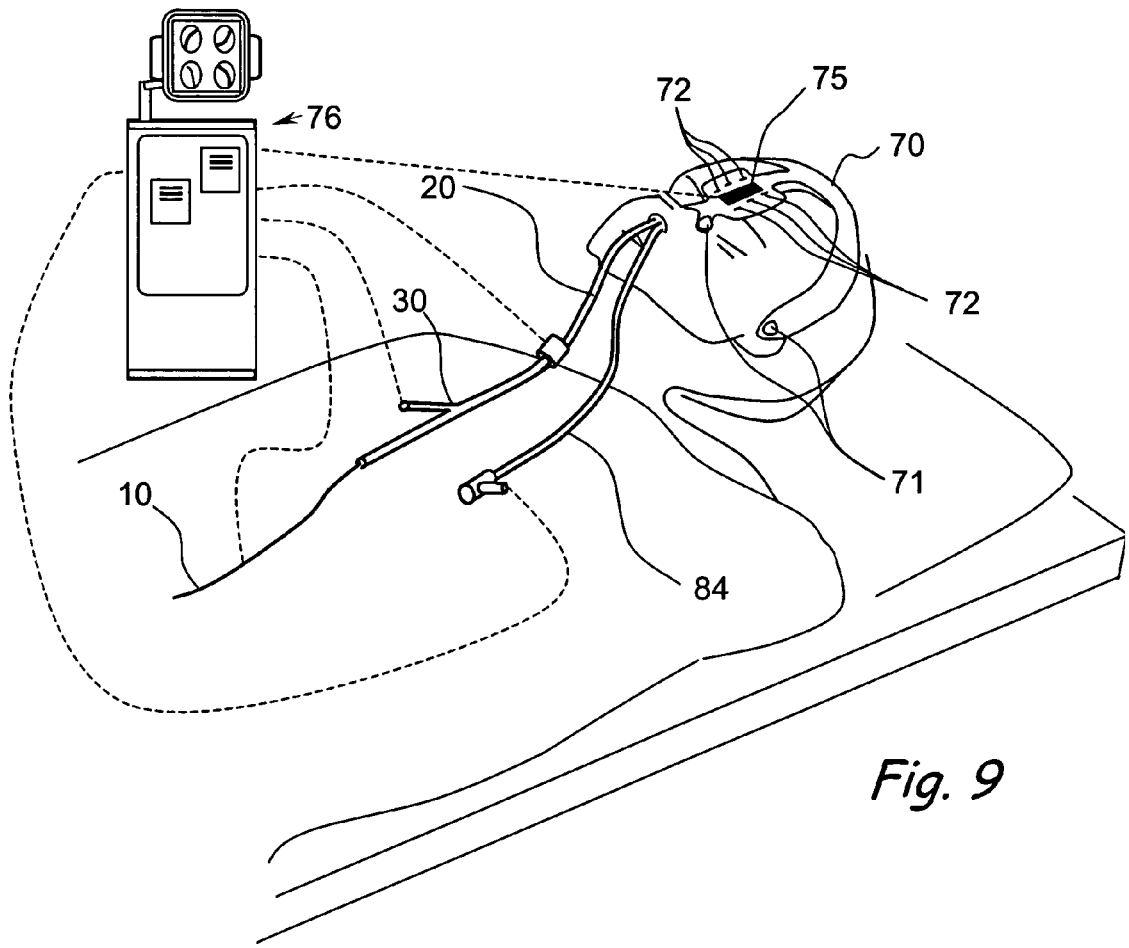
FIG. 9 shows the human subject positioned on the operating table during performance of an image guided interventional procedures using sensor equipped device(s) of the present invention.

Also, any of the sensor equipped working devices (e.g., guidewires, catheters, cannula, tubes, dilators, balloons, substance injectors, needles, penetrators, cutters, debriders, microdebriders, hemostatic devices, cautery devices, cryosurgical devices, heaters, coolers, scopes, endoscopes, light guides, phototherapy devices, drills, rasps, saws, etc.) may incorporate internal guidewire lumens for over-the-wire use or rapid exchange type guidewire lumens (e.g., tubes, split lumens or rails on that extend along a portion of the outer wall of the catheter) to facilitate rapid device and/or guidewire exchange during the procedure, unless the inclusion of such guidewire lumen would render the working device unusable for its intended purpose. In embodiments that incorporate a rapid exchange guidewire lumen (e.g., tubes, split lumens or rails on that extend along a portion of the outer wall of the catheter) such rapid exchange guidewire lumen may have a length of from about 0.5 cm through about 10 cm. In some embodiments, the guidewire lumen may have a distal aperture at the distal end of the device and a proximal aperture located less than 10 cm proximal to the distal aperture. The sensor equipped working devices of the present invention (e.g., guidewires, catheters, cannula, tubes, dilators, balloons, substance injectors, needles, penetrators, cutters, debriders, microdebriders, hemostatic devices, cautery devices, cryosurgical devices, heaters, coolers, scopes, endoscopes, light guides, phototherapy devices, drills, rasps, saws, etc.) may be used in conjunction with an image guidance system to perform a variety of image guided procedures for the treatment of sinusitis or other disorders of the paranasal sinuses, ears, nose or throat. An example of an electromagnetic image guidance system is shown in FIGS. 7-9. This image guidance system comprises a localizer apparatus 70 and a console 76 that includes a computer workstation 78 and a video monitor 80. As shown in FIGS. 7C and 7D, the video monitor 80 may be used in a single screen mode 80a to single screen image or in split screen mode 80b to simultaneously display 2 or more images.

Figure 8A:
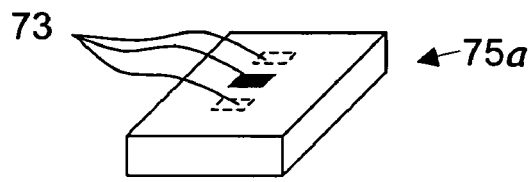
FIG. 8A is a perspective view of one embodiment of a localizer apparatus mountable transmitter having one or more transmitter locations.
Figure 8B:
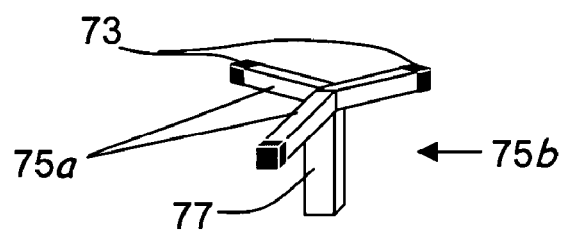
FIG. 8B is a perspective view of another embodiment of a localizer apparatus mountable transmitter having three transmitter locations.
Figure 8C:
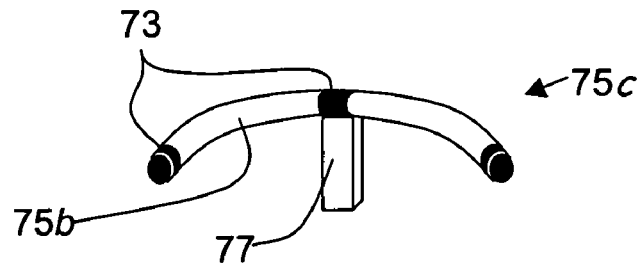
FIG. 8C is a perspective view of another embodiment of a localizer apparatus mountable transmitter having three transmitter locations.

The localizer apparatus 70, which in this example comprises a headset, has positioning projections 71 that are configured to rest on or to insert within the ear canals and on either side of the bridge of the subject's nose such that each time the localizer apparatus 70 is worn by the subject it will remain in the same substantially fixed position relative to the subject's paranasal sinuses and intranasal anatomy, even when the subject's head is turned or moved about. Two or more radiopaque fiducial markers 72 are mounted at fixed locations on either side of the portion of the localizer apparatus 70 that resides over the subject's forehead, as shown. Also, as seen in FIGS. 7E and 9, the localizer apparatus 70 is adapted to have a transmitter assembly 75 mounted at a specific location in the center of the portion of the localizer apparatus 70 that resides over the subject's forehead. As illustrated in FIG. 8, the transmitter assembly 75 has one or more transmitter locations or sites 73 which emit electrical signals that are sensed by the sensor(s) 16 located on the working devices that will later be inserted into the subjects nose. In some cases, such as that shown in FIG. 8A, a single transmitter 75a having single or plural (e.g., one, two, three or more) transmitter site(s) 73 may be used. If a single transmitter site 73 is used, the transmitter 71a may emit a variable signal from the single transmitter site 73 to create a non-uniform electromagnetic field such that the position of a single sensor 16 may be determined within that electromagnetic field. If three (3) or more transmitter sites 73 are used, the transmitter 75a may emit separate signals through each transmitter site 73 such that the location of an individual sensor 16 may be determined by a process of triangulation, similar to the manner in which GPS technology is used to determine the positions of objects on the earth's surface. In this regard, FIGS. 8B and 8C show alternative transmitters 75b, 75c, each of which has three (3) transmitter sites 73 at spaced apart locations which may be used for real time triangulation of the position of a single electromagnetic coil sensor 16 located on a working device 10, 20a, 20b, 30, 40, 60, etc. These transmitters 75a, 75b are constructed such that the transmission sites 73 are positioned on arm members 79a, 79b that emanate or extend from a central post 77, such arm members 75a, 75b being configured and positioned so as to provided the needed signal transmission while not obstructing the surgeon's access to the operative field.

Referring to FIG. 7A, in one example of an image guided FTSI procedure of this invention, the subject is initially placed in a CT scanner S while wearing the localizer apparatus 70 (without the transmitter 75 mounted thereon). A pre-procedure CT scan of the head is obtained using a protocol that Is compatible with the image guidance system to be used. After the pre-procedure CT scan has been completed, the CT scan data is down-loaded onto a transfer disc 82. Also, the pre-procedure CT scan may be used for planning of the procedure. During such planning, anatomical structures of interest (e.g., ostia and sinuses) may be identified and flagged, desired instrument trajectories may be plotted (e.g., the surgeon may plan the trajectory on which a curved penetrator 60 will be advanced to create openings in or between the ethmoid air cells) and "keep out" areas may be defined (e.g., skull base, posterior/superior wall of sphenoid near pituitary, orbital floor, facial nerves, etc.)

As shown in FIG. 7B, before beginning the FTSI procedure, the CT scan data is uploaded from the transfer disc 82 into the computer 78 of the image guidance system.

With reference to FIG. 7E, the localizer apparatus 70 is again placed on the subject's head and a transmitter 75 is attached to the localizer apparatus 70. The positioning projections 71 are placed in the same locations as during the pre-procedure CT scan, thereby ensuring that the localizer apparatus 70 and its fiducial markers 72 are in the same positions relative to the subject's head as they were during the pre-procedure CT scan. The transmitter 75 is connected to the computer 78. In accordance with its programming, the computer 78 then initiates and performs a localization protocol to accomplish the "registration" process whereby the positions of the fiducial markers 72 are used to correlate the stored CT scan data with the subject's current body position. Such localization protocol may require the physician to touch the tip of a sensor equipped working device 30 or a non-sterile sensor equipped localization wand to each fiducial marker and signaling to the computer 78 when such is accomplished, thereby enabling the computer to correlate the current positions of each fiducial marker 72 within the electromagnetic field with the position of that fiducial marker 72 on the stored CT scan images.

With reference to FIG. 9, the sensor equipped tubular guide 20 may be initially inserted into the subject's nose and the sensor lead wires 14 of the tubular guide 20 connected to the console 76. The sensor equipped tubular guide 20, as well as the other sensor equipped working devices 30, may be pre-calibrated at the point of manufacture. Calibration details (e.g., length of instrument, position of sensor relative to distal tip, baseline output from additional sensors, etc.) may be stored in an electronically readable medium (e.g., a read-only tag) on or in each working device 30 such that, when each working device 30 is connected to the console 76 or a precalibrated handpiece, the computer 78 will read the calibration tag and will cause the image guidance system to self-calibrate accordingly. The sensor(s) 16 of the tubular guide 20 receive signals from the transmitter site(s) 76 and in turn send signals to the computer 78. The computer 78 uses such signals to determine the position of the sensor(s) 16 and/or the position of a desired portion (e.g., the distal tip) of the tubular guide 20 within the patient's body. The computer 78 also causes an indicator of the position of the sensor 16 and/or desired portion of the tubular guide 20 to appear on the video monitor 80 relative to the CT scan image displayed on the monitor 80. As the tubular guide 20 is advanced, the computer 78 will cause the displayed CT scan image to scroll from cross section to cross section, thereby providing real time monitoring of the anatomical structures in the area of the sensor 16 and/or desired portion of the tubular guide 20. While viewing the position indicator and CT scan images on the monitor 80, the physician advances the tubular guide 20 to a position where its distal tip is adjacent to (and in substantial alignment with) a sinus ostium or other structure to be treated by a working device 30.

A non-sensor equipped or sensor equipped guidewire may then be advanced through the tubular guide 20 into or through the sinus ostium or other area to be treated by the working device 30. In some cases, the guidewire may be initially inserted within the lumen of the tubular guide 20 and may be advanced along with the tubular guide 20. In other cases, the tubular guide 20 may be inserted first and the guidewire may subsequently be advanced through the lumen of the tubular guide 20. In the particular example shown in FIG. 9, a sensor equipped guidewire 10 is used. The sensor lead wires 14 of the sensor equipped guidewire 14 are attached to the console 76 and the computer 78 performs the self-calibration in the same manner as described above. After the self-calibration for the guidewire 10 has been completed, the guidewire is advanced as the sensor(s) 16 on the guidewire 10 receive signals from the transmitter site(s) 76 and in turn the sensor(s) 16 send signals to the computer 78. The computer 78 uses such signals to determine the position of the guidewire's sensor 16 and/or a desired location on the guidewire 10 (e.g., its distal tip). The computer 78 also causes an indicator of the position of the sensor 16 and/or desired portion of the guidewire 10 to appear on the video monitor 80 relative to the CT scan image displayed on the monitor 80. In some cases, while the tubular guide 20 and guidewire 10 are both positioned within the subject's body, the monitor 80 will display indicators of the positions of both the tubular guide 10 and guidewire 20. In other cases, once the tubular guide 20 has been advanced to its intended position, the indicator of tubular guide 20 position may be deactivated so that it no longer appears on the monitor 80 and the only device position indicator appearing will then be that of the guidewire 10. In cases where position indicators for two or more working devices 30 (e.g. a tubular guide 20 and a guidewire 10 are simultaneously displayed on the monitor 80, the position indicators may be color coded or otherwise made to be distinguishable from one another. If more than one sensor-equiped device is placed in the anatomy, the surgeon (or system) must choose which device is the "master" (the device whose movement controls the position of the cross hairs and therefore which image slices are displayed) and which device is the "reference" (ie, its relative position is displayed, but movement of this device does not move the cross hairs or change which image slices are displayed. In some applications, it may be desirable to advance the guidewire 10 into a sinus or other cavity such that the guidewire 10 becomes coiled within that cavity. If the body of the guidewire is radiodense, such coiling of the guidewire within the sinus or other cavity may be used as a means to enhance visualization of the cavity by fluoroscopy or other radiographic means. In this regard, it is to be appreciated that the guidewire 10 could be equipped with a plurality of sensors 16, such that a primary sensor 16 is located at or near the distal tip and one or more secondary sensors are located along the shaft of the guidewire 10. The primary sensor 10 could remain active while the secondary sensors could be actuated and deactuated on demand. This would enable the physician to confirm that a sufficient amount of the guidewire 10 has been advanced into or past a particular anatomical location (e.g., confirm that enough of the guidewire 10 has been advanced into and coiled within a paranasal sinus.

After the guidewire 10 has been advanced to its desired position (e.g., where the distal portion of the guidewire 10 extends through the sinus ostium or other area to be treated), the sensor equipped working device 30 is inserted over the guidewire 10. In some cases, the tubular guide 20 may remain in place and the sensor equipped working device 30 will be inserted over the guidewire 10 and through the tubular guide 20, as shown in the example of FIG. 9. In other cases, the tubular guide 20 may be removed leaving the guidewire 10 in place and the working device 30 may then be inserted over the guidewire 10 alone. The sensor lead wires 14 of the sensor equipped working device 30 are attached to the console 76. The computer 78 performs a self-calibration as described above. After the self-calibration for the sensor equipped working device 30 has been completed, the sensor equipped working device 30 is advanced over the guidewire 10. As the working device 30 is advanced, the computer 78 receives signals from the transmitter site(s) 76 and sensor(s) 16 on the working device 30. On the basis of such signals, the computer 78 will cause one or more indicator(s) of the position of the working device 30 to appear on the video monitor 80 relative to the CT scan image displayed on the monitor 80. While viewing the video monitor, the physician may advance the working device 30 to a precise location within the body where its working element 36 is operatively positioned within the sinus ostium or other area to be treated. It will be appreciated that in some embodiments, a one or more sensor(s) 16 may be positioned on the working device 30 so as to delineate or mark the location of its working element 36 (e.g., sensors may be located at the proximal and distal ends of a dilation balloon or a single sensor may be positioned a known distance form the distal tip of a penetrator), thereby facilitating precise positioning of the working element 36 relative to the sinus ostium or other anatomical area to be treated by the working element 36. In some cases where other sensor equipped devices (e.g., the tubular guide 20 and guidewire 10) remain positioned within the subject's body along with the working device 30, the monitor 80 may display indicators of the positions of some or all of those other devices along with the indicator of the position of the working device 30. In other cases, the position indicator(s) of the other devices may be deactivated or caused not to be displayed on the video monitor 80 so that only the position of the working device 30 is visible. In other cases, the position indicator for the working device 30 may be displayed simultaneously with position indications of the other indwelling sensor equipped devices (e.g. tubular guide 20 and guidewire 10) and the position indicators for each of the separate devices may be color coded or otherwise distinguishable from one another when viewed on the monitor 80.

In some procedures, more than one working device 30 may be used. Accordingly, in such procedures, after one working device has been used to deliver a desired treatment or portion of a treatment (e.g., a balloon used to dilate the ostium of a paranasal sinus), that first working device may be removed, leaving the guidewire 30 in place. Thereafter, another working device 30 may then be advanced over the guidewire 30 and used to deliver another stage of the treatment to the same location. Or, the guidewire 10 may be moved to a different location and another working device 30 (or even the same working device 30) may then be used to deliver a treatment to a different treatment location. This may be repeated numerous times with various different types of working devices 30. For example, in some FTSI procedures, a first working device 30 in the form of a balloon dilation catheter 40 may be advanced over the guidewire 10, used to dilate the ostium of a paranasal sinus and then removed, leaving the guidewire 10 in place. Thereafter, a second working device in the form of a penetrator 60 may be advanced over the guidewire 10 into the paranasal sinus and used to puncture a mucocele, mucocyst or other vesicle located on the wall of the sinus or elsewhere. The penetrator 60 may then be removed leaving the guidewire 10 in place. Thereafter, another working device 30 in the form of a tube or sheath 50 may be advanced over the guidewire 30 and used to lavage (e.g., wash out) the sinus. After the lavage is complete, the tube or sheath 50 may be removed, leaving the guidewire 10 in place, and yet another working device in the nature of a substance eluting implant delivery catheter may be advanced over the guidewire 10 and used to place a substance eluting implant (e.g., a therapeutic implant as described in incorporated U.S. patent application Ser. Nos. 10/829,917 and 10/912,578) in or near the affected paranasal sinus. After all of the desired working devices 30 have been inserted and used, the guidewire 30 (and the tubular guide 20 if it remains at that point) may be withdrawn and removed from the subject's nasal cavity.

Figure 9A:
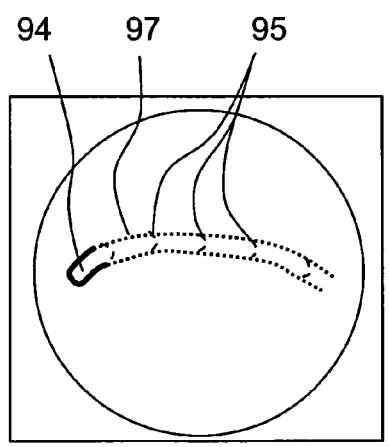
FIG. 9A is a schematic showing of a video monitor displaying indicia of the path of advancement or movement of a sensor equipped working device in accordance with the present invention.
Figure 13A:
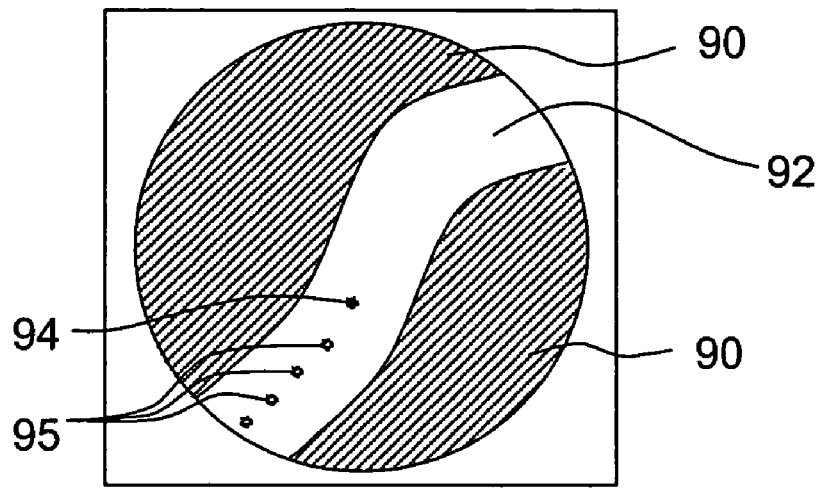
FIGS. 13A and 13B are schematic showings of examples of anatomical images viewed on a video monitor with indicia of the current position and prior path of advancement of an image guided working device shown in relation to a) adjacent anatomical structures and b) "keep in" and/or "keep out" zones that have been delineated to assist the operator in safely and correctly performing the procedure.
Figure 13B:
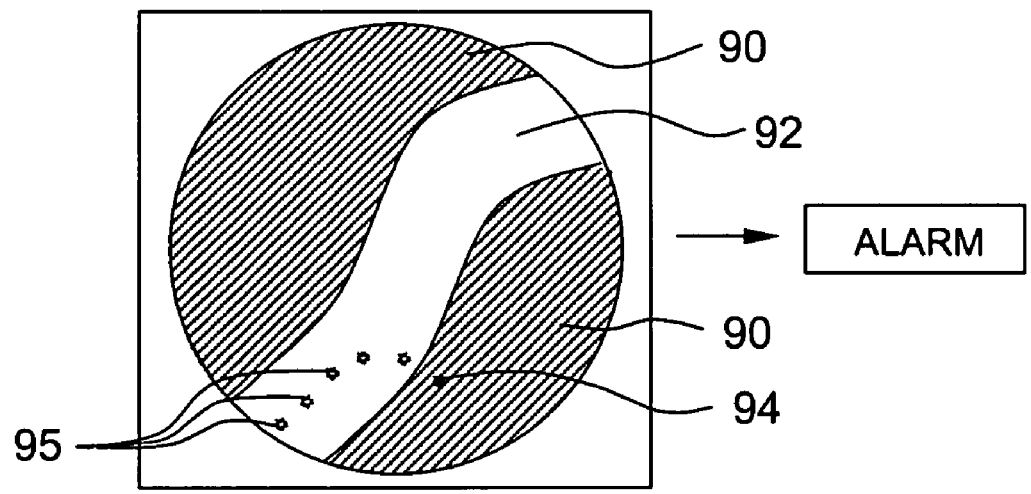

With reference to FIGS. 9A and 13A-B, the computer 78 may be programmed to display on the video monitor 80 not only an indicator 94 of the current position of a sensor equipped device 10, 20, 30, 40, 50, 60, 220 but also path indicator(s) 97 (e.g., ghosts, dotted lines, etc.) indicating the prior positions (e.g., the path of advancement) of that sensor equipped device 10, 20, 30, 40, 50, 60, 220 such that the device's path of advancement or retraction can be visualized on the monitor 80. Optionally, some distance measurement markings 95 (e.g., hash marks) may also be displayed to allow the physician to easily determine the relative distance by which a sensor equipped device 10, 20, 30, 40, 50, 60, 220 is advanced or retracted. Alternatively or additionally, the computer 78 may optionally be programmed to display path indicator(s) 97 indicating a planned path of device advancement that is intended to be followed.

Also, optionally, the computer 78 may be programmed such that, as a sensor equipped device 30 is advanced or moved over a particular path, that path may be converted into a different type of indicia (e.g., a solid or color coded line) and displayed on the video monitor 80. In this regard, the tip of a sensor-equipped working device 30 could be advanced, passed or swept over an anatomical surface or boundary and the computer 78 could then cause the monitor 80 to display an indication (e.g., a solid or colored line) delineating or demarcating that anatomical surface or boundary. This aspect of the invention could be used, for example, to provide on the displayed video image an outline of the inner surface of a paranasal sinus. Also, for example, this aspect of the invention could be used intraoperatively to provide a current image of the shape of an anatomical structure that is being modified in the procedure (e.g., the shape of the nasal septum during a septoplasty procedure intended to straighten the septum). Similarly, by changing a setting on the computer, the surgeon could trace with the distal tip of the sensor-equipped device the boundary of anatomical structures to be "erased" from the displayed images.

It is to be appreciated that, in some procedures of the present invention, other types of imaging such as fluoroscopy or x-ray may be used as well as the image guidance system 76. Thus, the device so the present invention may include one or more radiopaque markers or radiographically visible region(s) to facilitate their use with fluoroscopy or x-ray.

Also, optionally, the computer 78 of the image guidance system may be programmed to accept operator input as to points or locations along a path of device advancement that should be tagged or flagged on the displayed image and/or on a recorded image maintained as a record of the procedure. These tags can then be correlated with the image guidance system so that as the physician reviews the case on the CT, the endoscopic images are linked and being "flown through" as well.

Optionally, in some procedures, it may be desirable to also insert an endoscope 84 within the subject's body to obtain an endoscopic image that may be viewed separately or concurrently with the pre-procedure scan images and indicia of device position indicators 97, 97, 95 provided on the video monitor 80. When so employed, the endoscope 84 may or may not be equipped with sensor(s) 16 to allow its position to be monitored by the image guidance system. Standard endoscopes used during functional endoscopic sinus surgery (FESS) may be used for this purpose, including but not limited to the Karl Storz Hopkins II rigid scope (7210AA) and the Karl Storz Flexible Rhino-Laryngoscope (11101RP) which are available commercially from Karl Storz Endoscopy—America, Culver City, Calif. In cases where the endoscope 84 is equipped with one or more sensor(s) of its own, the sensor(s) mounted on the endoscope will provide a real time indication of the position of the endoscope 84 within the subject's body. In cases where the endoscope 84 is not equipped with sensor(s) 16, another sensor equipped guidewire 10 or device 30 may be inserted into the endoscope 84 to provide an indication of the endoscope's location within the body. For example, a non-sensor equipped endoscope 84, such as a flexible endoscope (e.g., Karl Storz Flexible Rhino-Laryngoscope (11101 RP), Karl Storz Endoscopy—America, America, Culver City, Calif.), may be used and a sensor equipped guidewire 10 may be inserted into (e.g., "parked" within) the working lumen of that endoscope 84. In this manner, the sensor(s) 16 on the guidewire will provide to the computer indicia of the position of the endoscope 84 as it is navigated through the anatomy. In this manner, an indicator of the position of an endoscope 84 (or any other device into which the sensor equipped guidewire 10 may be inserted) may be displayed on the image guidance system monitor 80, even though that endoscope 84 (or other device) is not itself equipped with a sensor 16. A window or signal transitionable region may be formed in the endoscope to allow the sensor(s) on the guidewire 10 to receive signals from the transmitter 75, or the portion of the guidewire 10 on which the sensor(s) is/are located my protrude out of an opening in the endoscope to allow the sensor(s) on the guidewire 10 to receive signals from the transmitter 75. It is to be appreciated that this procedure is useable not only with endoscopes 84, but also with any other devices into which a sensor-equipped guidewire 10 may be inserted. For example, a sensor equipped guidewire 10 may be inserted into a needle and used to guide the needle to a desired submucosal position where it is desired to deliver a substance (e.g., a drug or other therapeutic substance) or implant.

In some procedures where an endoscope 84 is employed, the visual image obtained from the endoscope 84 may be displayed on a monitor that is separate from the image guidance system monitor 80 (e.g., on a separate endoscopic tower commonly used with endoscopes during FESS). In other instances, the endoscopic image may be displayed on the image guidance system monitor 80 interchangeably with the pre-procedure scan images and indicia of device position indicators 97, 97, 95 (e.g., such that the physician may switch back and forth between a real time, line-of-sight image provided by the endoscope 84 and the pre-procedure scan images and device position indicators 97, 97, 95 provided by the image guidance system. In other instances, the image guidance system may incorporate two separate monitors 80, one of which displays a real time, line-of-sight image provided by the endoscope 84 and the other of which displays the pre-procedure scan images and device position indicators 97, 97, 95 provided by the image guidance system. In still other instances, the image guidance system may incorporate a single monitor 80 that is operable in split screen mode such that one portion of the monitor screen displays a real time, line-of-sight image provided by the endoscope 84 and another portion of the monitor screen displays the pre-procedure scan images and device position indicators 97, 97, 95 provided by the image guidance system. In yet other instances, the computer 78 of the image guidance system may be programmed to combine or integrate a real time, line-of-sight image that is received from the endoscope 84 with the stored pre-procedure scan images or with computer models that have been derived from the pre-procedure scan images and loaded into the image guidance system computer 78.

Figures 10A, 10B:
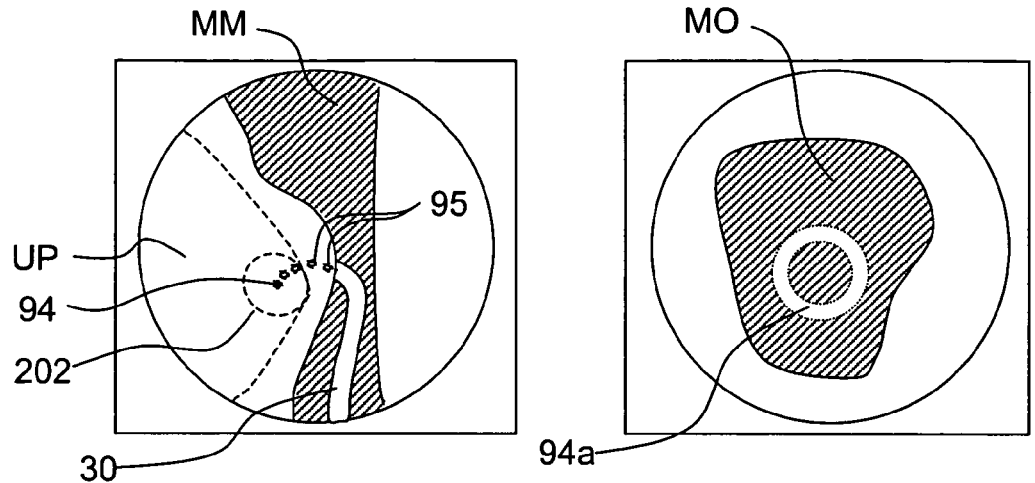
FIG. 10A shows a first orthogonal view of an anatomical image with indicators of the current position of the distal tip of a working device and indicia of the path of advancement of that working device, as seen on a video monitor screen during performance of a procedure according to this invention.
FIG. 10B shows a second orthogonal view of the procedure shown in FIG. 10A as viewed on a separate video monitor screen during performance of a procedure according to this invention.

FIGS. 10A and 10B show one example of the manner in which an endoscopic image may be used in conjunction with CT scan images to provide unique displays and images to the physician. In this example, a standard rigid endoscope is used. Typically, before the endoscope is inserted, a vasoconstricting agent e.g., cocaine, ephedrine, etc.) is sprayed into the nose. The endoscope 84 is then inserted into the nares and positioned to view the medial meatus MM, which is an open passageway adjacent to the middle turbinate MT. The uncinate process UP is a rigid structure that protrudes from the lateral wall of the nose, near the anterior end of the middle turbinate, preventing the endoscope 84 from viewing structures that lie behind the uncinate process UP. Such structures include the ethmoid bulla and an opening called the hiatus semilunaris as well as the ostium of the maxillary sinus which drains into the hiatus semilunaris. Thus, in typical FESS procedures, it is necessary for the physician to surgically incise or remove the uncinate process UP in order to view or insert rigid instruments into the ethmoid bulla, hiatus semilunaris or ostium of the maxillary sinus. However, in the example of FIG. 10A, the computer 78 of the image guidance system has used the stored CT scan data to integrate, into the displayed endoscopic image, an anatomical structure indicator 202 (e.g., a dotted line or other demarcation) showing the position of an anatomical structure of interest that is hidden from view of the endoscope 84 by the protruding uncinate process UP and/or portions of the midal turbinate MT. In the particular example of FIG. 10A, the anatomical structure indicator 202 is in the form of a generally circular dotted line showing the perimeter of the maxillary sinus ostium MO. A flexible sensor equipped working device 30 is being advanced through the medial meatus MM, around the intact uncinate process UP and into the maxillary ostium MO, as indicated by a device position indicator 94 and advancement path indicators 95.

As shown in FIG. 10B, in this example a separate video screen displays a sagital tomographic image of the maxillary ostium MO based on the pre-procedure CT scan images that are stored in the computer 78 of the image guidance system. The computer 78 is programmed to cause an indicator 94b of the position of the distal end of the working device 30 relative to the maxillary ostium MO. In this example the indicator 94b is a circle, but any suitable marking or demarcation may be used. This view shown in FIG. 10B aids the physician in advancing the distal end of the working device 30 through the maxillary ostium MO, without having to incise or remove the uncinate process UP.

Also, in some embodiments of the invention, the computer 78 may be programmed to use the distal tip of the guidewire 10 or any other location on any other working device 30 as a "virtual viewpoint" from which a virtual endoscopic view is created from the pre-procedure CT scan images and displayed on the monitor 80.

Also included in the present invention are systems and methods for performing endoscopic medical or surgical procedures anywhere in the body of a human or animal subject. For example, an endoscope 84 having an electromagnetic sensor 16 thereon may be advanced though a portion of the subject's body while the image guidance system computer 78 receives and uses signals received from the sensor 16 on the endoscope 84 to determine the position of the endoscope within the subject's body, stores endoscopic images received from the endoscope and correlates the stored endoscopic images with locations within the subject's body. Thereafter, the operator may request an endoscopic image obtained from a specified location within the subject's body and the computer 78 may display on the video monitor 84 the stored endiscopic image obtained at the selected location. In some cases, the selected location may be the current location of a working device 30 within the subject's body. In this regard, a working device 30 that has an electromagnetic sensor 16 thereon may be positioned within the subject's body, the computer 78 may determine the position of the working device based on signals received from the sensor on the working device 30 and the computer 78 may display on the video monitor a stored endoscopic image that was previously obtained from the current location of the working device 30.

In this manner, the operator is provided with an endoscopic image of the anatomy near the working device even though the working device may not be equipped with an endoscope. In other cases, this system and method may be used to compare a real time endoscopic image to a previously stored endoscopic image. For example, an endoscope 84 having a sensor 16 thereon may be positioned within the subject's body and used to obtain a real time endoscopic image. The computer 78 may use signals received from the sensor 16 on the endoscope 84 to determine its real time position and to display a real time endoscopic image obtained from the endoscope currently positioned within the body and ii) a stored endoscopic image that was previously obtained at the same location where the endoscope 84 is currently positioned. The real time and stored endoscopic images may be displayed side by side (e.g., on separate screens or using a split screen on a single monitor 84. This technique may be used, for example, to compare a post-operative or intra-operative endoscopic image to a previously obtained pre-operative endoscopic image for the purpose of assessing efficacy, changes, etc.

The computer 78 of the image guidance system may also be programmed to display on the image guidance system monitor 80 and/or on a separate endoscopic monitor, one or more virtual images generated from the stored CT scan data and/or the device position data received from the sensor(s) 16. For example, virtual images of ostia, bones and portions of devices (e.g., inflated balloons) that are not visible on a displayed endoscopic image. Examples of this are shown in FIGS. 11A-11C.

Figures 11A, 11B, 11C:
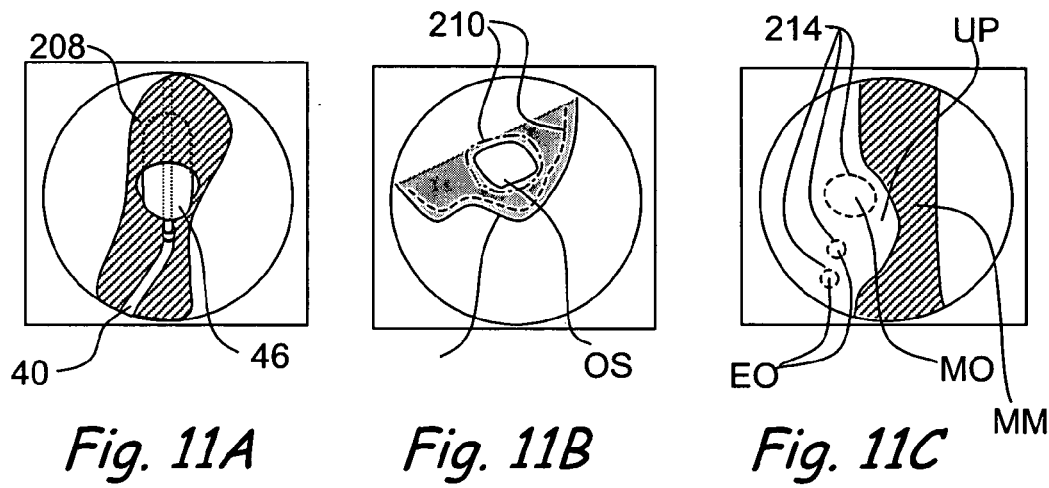
FIGS. 11A-11C show examples of direct line-of-sight endoscopic images with superimposed indicia indicating the positions of anatomical structure(s) and/or apparatus that are hidden from view on the line-of-sight endoscopic images, as viewed on video monitors during performance of procedures according to this invention.

FIG. 11A shows an image obtained from an endoscope 84 wherein an image guided dilation catheter 40 having a dilation balloon 46 has been advanced partially through an anatomical opening 209 and the balloon has been inflated. In this example, the computer 78 is programmed to use the information received from the sensor(s) on this balloon dilation catheter 40 to superimpose or otherwise display on the endoscopic image a virtual image (e.g., dotted line) 208 representing the portion of the inflated balloon 46 that is hidden from actual view of the endoscope.

FIG. 11B shows an image obtained from an endoscope 84 viewing an anatomical structure AS within the body. This particular anatomical structure AS is made up of bone covered with mucous membrane or other soft tissue, as is typical of structures located within the nose and paranasal sinuses. An ostium OS or opening is formed in the anatomical structure AS, as shown. In this example, the computer 78 is programmed to use information from the stored pre-procedure CT scan data to superimpose or otherwise display, on the endoscopic image, virtual images (e.g., dotted lines) 210 showing the edges of the bones that underlie the anatomical structure AS and ostium OS being viewed by the endoscope 84.

FIG. 11C shows an image obtained from an endoscope 84 positioned within the middle meatus MM, anterior to the uncinate process UP. In this example, the computer 78 is programmed to use information from the stored pre-procedure CT scan data to superimpose or otherwise display, on the endoscopic image, virtual images (e.g., dotted lines) 214 showing the maxillary ostium MO and openings into the ethmoid air cells EO, which are hidden from the endoscope's view by the uncinate process UP. The ability to view virtual images 214 of the maxillary ostium MO and/or openings into ethmoid air cells EO may enable the physician to advance flexible or curved devices (e.g., the guidewires, catheters, penetrators and any other working devices 30) into or through those openings MO, EO to perform treatment procedures directed at the maxillary sinuses and/or ethmoid air cells without requiring removal or surgical modification of the protruding uncinate process UP. An example of a procedure for dilation the maxillary ostium and/or delivering other treatment to the maxillary sinus is described above. Various other procedures may be performed to treat or ablate the ethmoid air cells. Some examples of the types of procedures that may be performed to treat and/or ablate the ethmoid air cells include those described in U.S. patent application Ser. No. 11/037,548 which is incorporated herein by reference.

Figure 12:
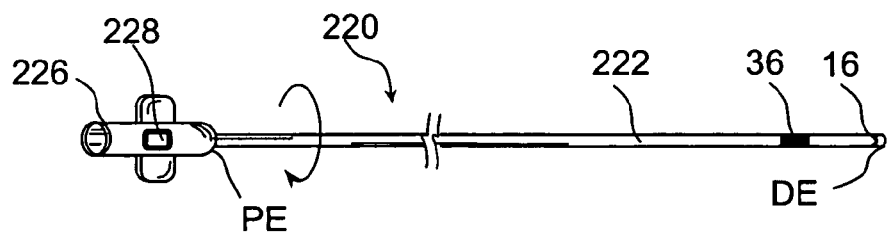
FIG. 12 shows a sensor-equipped working device of the present invention that is additionally equipped with a rotation sensor to indicate the rotational orientation of the device while it is positioned within a subject's body.

Also, any of the working devices 10, 20, 30, 40, 50, 60 of the present invention may include, in addition to one or more of the image guidance system sensors 16, one or more other sensors or movement indicators that may provide further information regarding the 3 dimensional position and/or orientation of the device 10, 20, 30, 40, 50, 60. The types of other sensors or movement indication apparatus that may be used include, for example, accelerometers, strain gages (for flexible instruments), pitch/roll sensors, and capacitive sensors. FIG. 12 shows one example of a working device 220 (e.g., a guidewire, catheter, cannula, tube, dilator, balloon, substance injector, needle, penetrator, cutter, debrider, microdebrider, hemostatic device, cautery device, cryosurgical device, heater, cooler, scope, endoscope, light guide, phototherapy device, drill, rasp, saw, etc.) that comprises an elongate shaft 222, a hub member 226 located on the proximal end PE of the shaft, an image guidance sensor 16 (e.g., an electromagnetic coil) located on the shaft 222 at a known distance from its distal end DE and a working element 36 (e.g., a dilator, balloon, injector, light delivery lens, endoscopic lens, cutter, opening, port, heater, cooler, probe, or other treatment delivering aparatus or structure). All or portion(s) of the shaft 222 may be rigid, flexible or malleable. An accelerometer 228 is mounted on one side of the hub 226, as shown. This accelerometer 228 sends signals to the computer 78 indicating rotational movement of the device 220. The computer 78 is programmed to process those signals and to provide, on the basis of those signals, an indicator of the current rotational orientation of the device 220 within the subject's body. In operation, as the device may be inserted into the subject's nostril with a specific maker (not shown) or structure (e.g., one or more wings 227) of the device 220 in specific radial orientation (e.g., such that the wings 227 on the hub 226 extend vertically up and down—at the 12 o'clock and 6 o'clock positions). A foot pedal or button on the console 76 may be depressed to cause the computer 78 to identify the current position of the accelerometer 228 as the "zero" or starting position. Thereafter, any clockwise or counterclockwise rotation of the device 220 will cause signals to be sent from the accelerometer 228 to the computer 78 and the computer will cause indicia of such rotational movement of the device 220 to be shown on the monitor 80 or elsewhere.

The present invention is also useable to aid the operator in maintaining the operative instruments within predefined areas of the subject's body (e.g., "keep in zones") and/or to avoid advancing operative instruments into other predefined areas of the subject's body (e.g., "keep out zones"). Examples of this are shown in FIGS. 13A and 13B. As shown, the computer 78 may be programmed to display indicia (e.g., shaded and unshaded areas) demarcating keep out zones 90 and a keep in zone 92. The intended keep in zone(s) and keep out zone(s) may be electronically marked on the CT scan images during the physician's pre-procedure planning. As shown in FIG. 13A, as a sensor equipped working device 30 of the present invention is advanced or moved within the keep in zone 92, device position indicators 94 and path indicators 95 will appear only within the keep in zone 92 and no alarm (e.g., visual or audible alarm) will be provided to the operator.

However, as shown in FIG. 13B, if the working device 30 is advanced or moved into either of the keep out zones 90, the device position indicator 94 will appear in the keep in zone 92 and, optionally, the computer 78 may be programmed to cause an alarm (e.g., visual or audible alarm) to be provided to the operator.

In some cases, it may be possible to maintain the subject's head in a substantially fixed position during the procedure. In those cases, the transmitter assembly 75 need not be mounted on a localizer apparatus 70 or otherwise affixed to the subject's head. Instead, in such cases, it may be possible for just the fiducial markers 72 to be affixed to the subject's body while the transmitter assembly 75 and fiducial markers 72 may be mounted on or within the operating table, on a nearby IV pole, on or in a fluoroscopic c-arm or elsewhere near the subject's body. However, in many image guided ENT procedures (including many FTSI procedures), it may be desirable to move or reposition the subject's head one or more times during the procedure. Also, in cases where the subject remains unanesthetized, it may be desirable to allow the subject to make some voluntary head movements during the procedure. Thus, it will often be desirable for the transmitter assembly 75 and fiducial markers 72 to be mounted on a localizer apparatus 70 or otherwise affixed to subject's body such that after the fiducial markers 72 have been used to perform the initial localization/registration protocol, the transmitter sites 73 will subsequently move in fixed spatial relationship to the subject's head. Certainly, a localizer apparatus 70 as shown in FIGS. 7E and 9 may be used for this purpose. However, such headset may be uncomfortable for an unanesthetized subject and/or may be an unwelcome or non-sterile obstacle located near the operative field during the procedure. Thus, the present invention provides other head attachment devices that may be used to attach the fiducial markers 72 and transmitter(s) 75 to the subject's head during the pre-procedure CT scan and also during the procedure. In some cases these head attachment devices may comprise adhesive patches that contain the fiducial markers 72 and to which the transmitter 75 is attachable. In other cases, a mouthpiece may be used as a head affixation device. Examples of such mouthpieces 240, 240a are shown in FIGS. 14A-15C.

In the embodiment shown in FIGS. 14A and 14B, a dental mouthpiece 242 is formed of silicon or other plastic. This mouthpiece 242 may be configured based on an impression of the subject's teeth such that the positioning of the mouthpiece 242 will be reproducible from wearing to wearing. The methods for making mouthpieces 242 of this type are well known and such mouthpieces are sometimes worn by athletes who play contact sports and by some individuals who tend gnash or grind their teeth during sleep. Radiopaque fiducial markers 244, such as metal articles, are mounted at locations on the mouthpiece 242, as shown. These fiducial markers 72 may be located on the buccal sides of the mouthpiece 242 so as to be easily accessible during the localization/registration protocol where it may be necessary for a sensor equipped device 30 or a sensor equipped wand to be touched against or placed in juxtaposition to each fiducial marker 72. A transmitter assembly 75 mounting location is provided on the mouthpiece such that the transmitter 75 may be attached to the mouthpiece 242 at a predetermined, reproducible position.

The embodiment 240a shown in FIGS. 15A-15C is the same as that shown in FIGS. 14A and 14B except that it includes a transmitter mounting member 244 that is attached to the front of the mouthpiece 242. The transmitter assembly 75 may be attached to this transmitter mounting member 244. Optionally, in some embodiments, a plurality of transmitter locations or sites 73 may be at spaced apart locations along the transmitter mounting member 73 to facilitate determination (e.g., by triangulation) of the position of a single sensor 16 positioned within the subject's ears, nose, throat or paranasal sinuses.

FIGS. 16 and 17 show examples of a cable connector assembly 400 that may be used in connection with any of the sensor equipped devices of the present invention, as well a other sensor equipped devices, to facilitae transmission of signal(s) between the sensor equipped device and an image guidance system, console 76 and/or computer 78. This cable/connector assembly 400 comprises a cable 402 one end of which is connected to the sensor equipped device and the other end of which terminates in a connector 402. The sensor leads 14 extend through the cable 402 to connector 404. A corresponding connector 406 is mounted on the image guidance system console 76 or computer 78. The connectors 404, 406 may comprise multi-pin connectors as shown, or any other suitable type of connector. In some embodiments, the connectors 404, 406 may transmit ither information or signals in addition to signals from the sensor(s) mounted on the device. For example, the sensor equipped device and/or connector 402 may contain a PROM, memory chip or other storage medium that holds magnetic or digitally encoded information relating to the device (e.g., calibration information, information relating the position of a sensor 16 to the distal end DE of the device, information relating the position of the sensor 16 to a working element on the device, information relating to the length, diameter or other sizing of the device, information as to the type of device (e.g., balloon catheter, guidewire, penetrator, cutter, tubular guide, etc.) being employed or numerous other types of information). That other information may be transmitted through certain prongs, pins, channels or other contact points in the connectors 404, 406 while the signals form the sensor(s) is/are transmitted through other prongs, pins, channels or other contact points in the connectors 404, 406. transmitted to the image guidance system console 76 and/or computer 78 and the connectors 404, 406.

With specific reference to FIG. 16, in some cases, an optional handpiece 408 may be attached to the end of the cable 402 opposite the connector 404. Such handpiece may perform the dual function of 1) connecting the cable 402 to the sensor equipped device and 2) providing a handpiece that the operator may use to manipulate, torque or otherwise move the device. In the particular example shown in FIG. 16, the proximal end of a sensor equipped guidewire 10 as shown in FIGS. 1-1A and described above, is inserted into a bore of the handpiece 408 causing the connector 21 on the proximal end of the guidewire body 12 to engage a corresponding connector (not seen in FIG. 16) located within the handpiece 408. In this manner, signals from the guidewire's sensor 16 will travel from the guidewire 10, through cable 402, to cable connector 404 and into console/computer connector 406, thereby providing communication between the guidewire 10 and the image guidance system console 76 and/or computer 78. When it is desired to advance another device over the guidewire 10, the handpiece may be disengaged from the proximal end of the guidewire to permit such advancement of another device over the guidewire.

With specific reference to FIG. 17, in cases where the handpiece 408 is not needed or desired, the cable 402 may be connected directly to the proximal portion of a sensor equipped device. In the particular example of FIG. 17, the cable 402 is attached to the proximal hub 38 of a working device 30 that is equipped with a working element 36 and sensor 16, as shown in FIG. 3 and described hereabove. The attachment of the cable 402 to the working device 30 may be permanent or disconnectable. In instances where the cable 402 is disconnectable from the device 30, a plug and jack arrangement may be used to allow the cable 402 to be volitionally connetd to and disconnected form the device 30.

FluoroCT is a relatively new technology in which a C-arm type three-dimensional (3D) imaging device (e.g., the ISO-C3D available from Siemens Medical Systems) is used to obtain a fluoroscopic computed tomogram. Because these C-arm devices may be mobile, Fluoro CT scans may be obtained intraoperatively and immediately postoperatively, as well as preoperatively. In some cases, FluoroCT may be used to obtain the pre-procedure imaging data stored in the image guidance system computer 78. Additionally, in some cases, one or more FluoroCT scans may be obtained during or after the procedure and data sets from such intraoperative or postoperative FluoroCT scans may be loaded into the computer 78. The computer 78 may be programmed to use such FluoroCT scan data to update the previously stored imaging data that has been obtained by traditional CT, MRI, FluoroCT or other means, thereby adjusting the stored anatomical image data to show changes to the anatomy that have occurred subsequent to the pre-operative scan. Additionally or alternatively, the computer may be programmed 78 to display the newly added FluoroCT data in addition to or in comparison with other images based on the preoperative scan, thereby allowing the surgeon to compare the current (e.g., intraoperative or postoperative) anatomy to the preoperative anatomy.

It is to be appreciated that the computer 78 of the image guidance system may be programmed with a number of optional programs (e.g., software bundles) to provide additional or different features. The following are non-limiting examples of some of the optional capabilities that may be programmed into the computer 78:

Device Path Suggestion Feature: The computer 78 may, in some embodiments, be programmed to automatically suggest path(s) of advancement or vector(s) along which a desired device (e.g., a sensor equipped working device 30) may be advanced to reach a desired location (e.g., the ostium of a particular paranasal sinus, the ethnoid air cells, a site of infection, a bulla, a mucocele, a mucocyst, etc.) The suggested path(s) of advancement or vector(s) may be selected based on operator-input criteria (e.g., least complex path, least tortuous path, least traumatic path, safest path, etc.) After it has determined the desired path(s) or vector(s) the computer 78 may cause indicia of such desired path(s) or vector(s) (e.g., dotted lines) to appear on the video monitor 80 in relation to the displayed anatomical CT and/or endoscopic images.

Path Ahead Mode: The computer 78 may, in some embodiments, be programmed to display not only the anatomical structures that are adjacent to or near the current position of a sensor equipped working device 30, but also anatomical structures that are located ahead on one or more path(s) on which the device 30 may be advanced from its current position to reach its target position. In this regard, the computer 78 may cause the monitor 80 to display 1) a tomographic section or other anatomical image of the area in which the working device 30 is currently located (the "current location image") and 2) one or more other tomographic sections or other images showing anatomical structures that lie ahead on one or more intended path(s) of advancement (the "path ahead image(s)). The current location image and the path ahead image(s) may be displayed simultaneously (e.g., on separate monitors, on a split screen monitor or on a single screen where with one image is inset within a larger image). Alternatively, current location image and the path ahead image(s) may be displayed one at a time such that the operator may switch back and forth between the current location image and the path ahead image(s).

Pre-Post Comparison Mode: The computer 78 may, in some embodiments, be programmed to take the stored pre-procedure imaging scan data and compare it to subsequently input a post-procedural or intra-operative imaging scan data such that the effects or anatomical changes caused by the procedure may be assessed.

Turn Cueing Mode: The computer 78 may, in some embodiments, be programmed to provide a turn indicator (e.g., an audible signal or visual indicator shown on the monitor screen) to indicate the direction that a guidewire 10 or other sensor equipped working device 30 should be turned to navigate toward a desired target location.

Treatment Forecastin—The computer 78 may, in some embodiments, be programmed to utilize the stored anatomical image data (e.g., CT scan data) to provides prompts or suggestions of 1) anatomical structures or pathological lesions that may be amenable to a particular treatment and/or 2) optimal or suggested locations and/or rotational orientations in which working device(s) 30 may be placed in order to effect a particular treatment and/or 3) the optimal or suggested size or dimensions of the working device(s) 30 to be used (e.g., for regions marked in red a 6 mm balloon diameter is suggested and for regions marked in blue a 7 mm balloon is suggested).

Simulation of Result—The computer 78 may, in some embodiments, be programmed to provide a simulated result of a particular procedure before the procedure is actually performed. The ability to generate a simulated result may be particularly advantageous in cases where it is not feasible for the physician to actually view the area being treated and, thus, is unable to make a visual assessment of such area as may be needed to arrive at an accurate prediction of the likely therapeutic and/or untoward results of a proposed treatment or maneuver. For example, the console 76 and computer 78 may be adapted to receive operator input of the particular diameter (or other dimensions/characteristics) of a dilator balloon that the physician proposes to use for dilation of a particular passageway. The computer 78 will be programmed with software that it will use to provide a simulated view of what that passageway would look like after it has been dilated by that proposed balloon and what submucosal, adjacent or hidden anatomical structures would likely be compressed or otherwise affected by such dilation procedure, if the procedure were actually performed using a balloon having the proposed diameter, dimensions and/or characteristics.

Simulation of Device—The computer 78 may, in some embodiments, be programmed to provide a simulated view of a particular device that is positioned within the subject's body. For example, the computer 78 may be programmed with device information (e.g., the dimensions, shape and appearance of the device) and, after tracking the trajectory of a the sensor 16 mounted on that device through the anatomy, the computer 78 may generate and display on the monitor 80, a "virtual" image of the device as it is positioned relative to the adjacent anatomy. This aspect of the invention may provide to the operator some "feel" for the relative 3 dimensional size and position of the device within the body.

Look Ahead Mode—The computer 78 may, in some embodiments, be programmed to provide a simulated view from a vantage point on a device that has been inserted into the subject's body. For example, the computer 78 may cause the monitor to display a forward looking view from the distal tip of an advancing guidewire as if the operator were sitting on the distal tip of the guidewire and looking forward at the anatomy as the guidewire is advanced.

Also, it is to be appreciated that any working device 30 may incorporate endoscopic components (e.g., fiber optic light guide, fiber optic image transmission bundle, lenses, etc.) as well as other working elements 36. In this regard, the working device 30 may comprise an on board endoscope that is useable to view some or all of the procedure wherein that working device 30 is employed. Alternatively, it is to be appreciated that any working device 30 may be inserted or incorporated into an endoscope such that the endoscope may be used to view some or all of the procedure wherein that working device 30 is employed.

Also, in any device or system described herein, the locations of the sensor(s) 16 and transmitter(s) 75 or transmitter sites 73 may be switched. For example, one or more transmitter sites 73 may be located on a transmitter equipped device (e.g., a guidewire, tubular guide, sheath, dilation catheter or other device having a working element as described herein) and one or more sensors 16 may be located on a localizer apparatus 70 such as a localizer frame or headset.

The use of the sensor equipped working devices 30 and methods of the present invention may serve a number of purposes and may provide a number of advantages over the prior art. For example, the use of such image guided devices and methods may permit very precise positioning and movement of devices within the subject's body, thereby improving the safety of the procedure, causing less trauma or unnecessary iatrogenic tissue modification, requiring less use of fluoroscopy or x-ray and hence less radiation exposure to the subject or the operator(s), etc.

It is to be further appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. All reasonable additions, deletions, modifications and alterations are to be considered equivalents of the described examples and embodiments and are to be included within the scope of the following claims.

What is claimed is:

1. A method for image guided performance of a treatment procedure to treat a disease or disorder of a paranasal sinus in a human or animal subject, said method comprising the steps of:
    A) providing a working device, at least a portion of said working device being insertable into a paranasal sinus of the subject and useable to carry out or facilitate at least a portion of said treatment procedure, a sensor being positioned at a location on the working device that is insertable into a paranasal sinus of the subject;
    B) providing an image guidance system that is useable to determine the location of the working device within the paranasal sinus of the subject on the basis of signals received from the sensor;
    C) inserting the working device such that the location is within an ear, nose, throat or paranasal sinus of the subject; and
    D) using the image guidance system to detect the position of the sensor within a paranasal sinus of the subject wherein the working device comprises a catheter or elongate member having an expandable dilator thereon;
    wherein the expandable dilator is sized and constructed to be positioned within the ostium of a paranasal sinus while in a non-expanded state and the thereafter be expanded to an expanded state, thereby enlarging the ostium;
    wherein the ostium in which the expandable dilator is to be positioned comprises a bone that underlies mucous membrane and wherein the expandable dilator is further constructed to exert sufficient force against the ostium to break bone that underlies the mucous membrane.

2. A method according to claim 1 wherein the sensor comprises an electromagnetic coil.

3. A method according to claim 1 wherein the working device has a distal end and wherein the location at which the sensor is positioned is in known relationship to the distal end of the working device such that the location of the sensor detected by the image guidance system will enable the operator to determine the position of the distal end of the working device within an ear, nose, throat or paranasal sinus of the subject.

4. A method according to claim 1 wherein the working device comprises a guidewire.

5. A method according to claim 1 wherein the working device comprises a flexible catheter.

6. A method according to claim 1 wherein the working device comprises a tubular guide.

7. A method according to claim 6 wherein the tubular guide comprises a proximal portion formed of a first material and a distal portion formed of a second material.

8. A method according to claim 7 wherein the proximal portion of the tubular guide is formed substantially of metal and the distal portion of the tubular guide is formed substantially of a polymer.

9. A method according to claim 6 wherein at least one curve is formed in the tubular guide.

10. A method according to claim 9 wherein the tubular guide has a distal end and wherein said at least one curve is configured to facilitate advancement of the distal end of the tubular guide into or near the ostium of a paranasal sinus.

11. A method according to claim 1 wherein the location at which the sensor is positioned is in known relationship to the position of the expandable dilator such that the location of the sensor detected by the image guidance system will enable the operator to determine the position of the dilator within an ear, nose, throat or paranasal sinus of the subject.

12. A method according to claim 11 wherein the expandable dilator has a proximal end and a distal end, and wherein the location at which the sensor is positioned is between the proximal and distal ends of the dilator.

13. A method according to claim 12 wherein the location at which the sensor is positioned is approximately midway between the proximal and distal ends of the dilator.

14. A method according to claim 11 wherein the location at which the sensor is positioned is in known relationship to at least one of the proximal and distal ends of the dilator such that the location of the sensor detected by the image guidance system will enable the operator to determine the position of at least one of a) the proximal end of the dilator and b) the distal end of the dilator, within an ear, nose, throat or paranasal sinus of the subject.

15. A method according to claim 1 wherein the expandable dilator comprises a balloon.

16. A method according to claim 15 wherein the working device comprises a balloon catheter.

17. A method according to claim 1 wherein the dilator is constructed to exert sufficient force to break bone adjacent to the ostium.

18. A method according to claim 17 wherein the dilator comprises a non-compliant balloon that is inflatable to an inflation pressure from about 10 atmospheres through about 30 atmospheres.

19. A method according to claim 1 wherein the working device comprises a tubular sheath.

20. A method according to claim 1 wherein the working device comprises an elongate penetrating member.

21. A method according to claim 20 wherein the elongate penetrating member comprises a needle.

22. A method according to claim 20 wherein the elongate penetrating member has a lumen extending longitudinally therethrough.

23. A method according to claim 1 wherein the working device has a treatment delivering location from which the treatment is delivered and wherein the sensor is positioned in known relationship to said treatment delivering location such that the location of the sensor detected by the image guidance system will enable the operator to determine the position of the treatment delivering location within an ear, nose, throat or paranasal sinus of the subject.

24. A method according to claim 23 wherein the a treatment delivering apparatus is located at the treatment delivering location, said treatment delivering apparatus comprising a device selected from the group consisting of a guidewire, catheter, cannula, tube, dilator, balloon, substance injector, needle, penetrator, cutter, debrider, microdebrider, hemostatic device, cautery device, cryosurgical device, heater, cooler, scope, endoscope, phototherapy device, drill, rasp, saw, punch, forceps and laser.

25. A method according to claim 1 wherein the working device is advanceable over a guidewire.

26. A method according to claim 1 wherein at least a portion of the working device is malleable.

27. A method according to claim 1 wherein at least a portion of the working device is flexible.

28. A method according to claim 1 wherein the image guidance system provided in Step A comprises i) a computer, ii) a video monitor, iii) a localizer and iv) a sensor tracking system.

29. A method according to claim 28 wherein anatomical image data has been obtained from the subject prior to performance of Steps C and D and wherein, prior to or during performance of Step D, the localizer is used to register the anatomical image data with the physical positioning of the subject's body.

30. A method according to claim 29 wherein at least one fiducial marker is affixed to or positioned in fixed relation to the subject's body while anatomical image data is obtained and wherein said at least one fiducial marker is also affixed to or positioned in fixed relation to the subject's body during performance of Step D and wherein the image guidance system uses the at least one fiducial marker during Step D to correlate the position of the subject's body with the sensor tracking system.

31. A method according to claim 30 wherein at least one fiducial marker is attached to an article that is worn by the subject during Step D.

32. A method according to claim 31 wherein the article comprises a headset.

33. A method according to claim 31 wherein the article comprises a mouthpiece.

34. A method according to claim 30 wherein the wherein at least one fiducial marker is affixed to the subject's body during Step D.

35. A method according to claim 34 wherein at least one fiducial marker is affixed to a tooth of the subject during Step D.

36. A method according to claim 30 wherein at least one fiducial marker is positioned within an ear canal of the subject during Step D.

37. A method according to claim 30 wherein the wherein the transmitter is affixed to the subject's body during Step D.

38. A method according to claim 30 wherein Step D comprises:
   causing the anatomical image data to be received by the computer; and, wherein,
   the computer causes the video monitor to display an anatomical image from the anatomical data along with an indicator indicating the location of the working device in relation to the anatomical image.

39. A method according to claim 38 wherein the computer i) receives working device location data from the sensor tracking system, ii) integrates the working device location data with the anatomical image data and iii) causes the video monitor to display an anatomical image along with an indicator indicating the position of the working device relative to the displayed anatomical image.

40. A method according to claim 38 wherein the anatomical image data comprises tomographic image data.

41. A method according to claim 38 wherein the anatomical comprises data obtained by CT or fluoroscopic CT scan.

42. A method according to claim 38 wherein the anatomical comprises data obtained by PET scan.

43. A method according to claim 38 wherein the anatomical image data includes data providing a plurality of orthogonal views of the subject's anatomy.

44. A method according to claim 43 wherein the orthogonal views include axial, coronal and sagittal views.

45. A method according to claim 30 wherein a plurality of fiducial markers are used.

46. A method according to claim 28 wherein the sensor tracing system comprises a transmitter that transmits a signal that is sensed by the sensor on the working device.

47. A method according to claim 46 wherein the transmitter is mounted on an article that is worn by the subject.

48. A method according to claim 47 wherein the article comprises a headset.

49. A method according to claim 47 wherein the article comprises a mouthpiece.

50. A method according to claim 28 wherein the sensor tracking system comprises an electromagnetic tracking system and wherein the sensor on the working device comprises an electromagnetic sensor.

51. A method according to claim 28 wherein:
   at least one fiducial marker is affixed to or positioned in fixed relation to the subject's body while an imaging scan is performed to obtain the anatomical image data;
   the anatomical image data is received by the computer;
   during Step D the at least one fiducial marker is affixed or positioned at substantially the same location relative to the subject's body as it was during performance of the anatomical imaging scan; and, wherein,
   during Step D the computer receives fiducial marker location data and uses that fiducial marker location data to perform a process of registration wherein the anatomical image data is correlated to the then current position of the subject's body as indicated by the fiducial marker location data.

52. A method according to claim 51 wherein the subject's head is moved during the treatment procedure.

53. A method according to claim 51 wherein the computer receives working device position data from the sensor tracking system and processes the working device position data with the fiducial marker location data to determine the current working device position relative to the anatomical image data.

54. A method according to claim 28 wherein the crosshairs are displayed on the video monitor to indicate the position of the working device relative to an anatomical image that is displayed on the same video monitor.

55. A method according to claim 28 wherein the computer is further programmed to define at least one zone selected from a) a keep in zone within which the working device is to remain and b) a keep out zone into which the working device is not to be advanced.

56. A method according to claim 1 wherein the image guidance system is further used to track a working device movement path during performance of Step D.

57. A method according to claim 56 wherein the image guidance system comprises a video monitor on which an anatomical image is displayed and wherein the working device movement path is displayed on the video monitor along with the anatomical image.

58. A method according to claim 57 wherein the working device movement path displayed on the video monitor includes an indicator of the current position of the working device along with at least one indicator of a past or intended future position of the working device.

59. A method according to claim 1 wherein the image guidance system receives a video image from an endoscope or endonasal camera positioned within an ear, nose, throat or paranasal sinus of the subject and displays that video image on a video monitor along with an indication of the location of the working device.

60. A method according to claim 59 wherein an imaging scan is performed prior to performance of Steps C and D to obtain a scanned anatomical image and wherein, during performance of Step D, the scanned anatomical image is displayed on a video monitor along with an indication of the location of the working device.

61. A method according to claim 60 wherein the video image and the scanned anatomical image are displayed on separate screens.

62. A method according to claim 60 wherein the video image and the scanned anatomical image are displayed on the same screen.

63. A method according to claim 62 wherein the video image and the scanned anatomical image are displayed such that one is superimposed on the other.

64. A method according to claim 62 wherein the video monitor displays the video image along with a hidden anatomical structure indicator, said hidden anatomical structure indicator indicating the location of at least one anatomical structure from the scanned anatomical image that is not directly visible on the video image.

65. A method according to claim 64 wherein the hidden anatomical structure indicator comprises solid or broken lines showing the outline of the hidden anatomical structure.

66. A method according to claim 64 wherein the hidden anatomical structure comprises the ostium of a paranasal sinus.

67. A method according to claim 66 wherein the ostium of a paranasal sinus is hidden from view on the video image by one or more other anatomical structures and wherein the hidden anatomical structure indicator shows the location of that ostium of a paranasal sinus.

68. A method according to claim 67 wherein the ostium of a maxillary sinus is substantially hidden from view by the uncinate process and wherein the hidden anatomical structure indicator shows the location of that maxillary sinus ostium.

69. A method according to claim 68 wherein the treatment procedure includes the transnasal insertion and advancement of a working device into or through the ostium of a maxillary sinus without removing or causing substantial trauma to the uncinate process.

70. A method according to claim 69 wherein the rotation sensor comprises an accelerometer or sensor positioned on the working device so as to detect rotation of the working device.

71. A method according to claim 67 wherein the ostium of a sphenoid sinus is substantially hidden from view by one or more ethmoid air cells and wherein the hidden anatomical structure indicator shows the location of that sphenoid sinus ostium.

72. A method according to claim 71 wherein the treatment procedure includes the transnasal insertion and advancement of a working device into or through the ostium of a sphenoid sinus without removing, altering or causing substantial trauma to the ethmoid air cells, middle turbinate, superior turbinate or supreme turbinate.

73. A method according to claim 67 wherein an ostium of a frontal sinus is substantially hidden from view by at least one of; a) the uncinate process, b) ethmoid bulla and c) middle turbinate, and wherein the hidden anatomical structure indicator shows the location of that sphenoid sinus ostium.

74. A method according to claim 73 wherein the treatment procedure includes the transnasal insertion and advancement of a working device into or through the ostium of a frontal sinus without removing or causing substantial trauma to the process, ethmoid bulla or middle turbinate.

75. A method according to claim 64 wherein an ethmoid bulla is substantially hidden from view by the uncinate process and wherein the hidden anatomical structure indicator shows the location of that ethmoid bulla.

76. A method according to claim 75 wherein the treatment procedure includes the transnasal insertion and advancement of a working device into or through an ethmoid bulla without removing or causing substantial trauma to the uncinate process.

77. A method according to claim 76 wherein the method further comprises the step of zeroing the accelerometer to establish a starting rotational orientation.

78. A method according to claim 64 wherein the hiatus semilunaris is substantially hidden from view by the uncinate process and wherein the hidden anatomical structure indicator shows the location of that hiatus semilunaris.

79. A method according to claim 78 wherein the treatment procedure includes the transnasal insertion and advancement of a working device into or through the hiatus semilunaris without removing or causing substantial trauma to the uncinate process.

80. A method according to claim 78 wherein the method further comprises causing the keep in zone or keep out zone to be identified on the video monitor.

81. A method according to claim 78 further comprising the step of providing an alarm signal to the operator when the working device exits or comes close to exiting a keep in zone.

82. A method according to claim 78 further comprising the step of providing an alarm signal to the operator when the working device enters or comes close to entering a keep out zone.

83. A method according to claim 64 wherein an ethmoid air cell is substantially hidden from view by at least one of; a) the uncinate process, b) ethmoid bulla and c) middle turbinate and, wherein the hidden anatomical structure indicator shows he location of that sphenoid sinus ostium.

84. A method according to claim 83 wherein the treatment procedure includes the transnasal insertion and advancement of a working device into or through an ethmoid air cell without removing, altering or causing substantial trauma to the uncinate process, ethmoid bulla or middle turbinate, superior turbinate or supreme turbinate.

85. A method according to claim 59 wherein the indication of the location of the working device comprises an indication of the location of at least a portion of the working device that is hidden from direct view of the endoscope or camera.

86. A method according to claim 1 wherein the working device further comprises a rotation sensor that generates a rotational orientation signal that indicates the rotational orientation of at least a portion of the working device within an ear, nose, throat or paranasal sinus of the subject and where the method further comprises the step of:

using the rotational orientation signal to detect the rotational orientation of at least a portion of the working device within an ear, nose, throat or paranasal sinus of the subject.

* * * * *